(12) United States Patent
Tan

(10) Patent No.: US 12,364,812 B2
(45) Date of Patent: Jul. 22, 2025

(54) KEEP VEIN OPEN INFUSION FLOW CONTROL DEVICE

(71) Applicant: CareFusion 303, Inc., San Diego, CA (US)

(72) Inventor: Benjamin Yang Teck Tan, Yew Mei Green (SG)

(73) Assignee: CareFusion 303, Inc., San Diego, CA (US)

( * ) Notice: Subject to any disclaimer, the term of this patent is extended or adjusted under 35 U.S.C. 154(b) by 237 days.

(21) Appl. No.: 17/851,608

(22) Filed: Jun. 28, 2022

(65) Prior Publication Data

US 2022/0323673 A1    Oct. 13, 2022

Related U.S. Application Data

(63) Continuation of application No. 16/862,308, filed on Apr. 29, 2020, now Pat. No. 11,400,210.

(51) Int. Cl.
  *A61M 5/168*    (2006.01)
  *A61M 5/142*    (2006.01)
  (Continued)

(52) U.S. Cl.
  CPC ........ *A61M 5/16813* (2013.01); *A61M 5/142* (2013.01); *A61M 5/16831* (2013.01);
  (Continued)

(58) Field of Classification Search
  CPC ........... A61M 2005/14208; A61M 2005/3125; A61M 2039/1083; A61M 2039/1088; A61M 39/10; A61M 39/285; A61M 5/142; A61M 5/16813; A61M 5/16831; A61M 2005/1404; A61M 39/26; A61M 39/28; A61M 39/284; A61M 39/286; A61M 5/14; A61M 5/141; A61M 5/16881;
  (Continued)

(56) References Cited

U.S. PATENT DOCUMENTS 4,668,217 A * 5/1987 Isono .................... A61M 39/10
                                                        604/29
4,976,590 A    12/1990 Baldwin
(Continued)

FOREIGN PATENT DOCUMENTS

EP        0270499 A2    6/1988
JP        H07507944 A   9/1995
(Continued)

OTHER PUBLICATIONS

International Search Report and Written Opinion for Application No. PCT/US2021/029465, dated Nov. 4, 2021, 27 pages.
(Continued)

*Primary Examiner* — Jason E Flick

(57) ABSTRACT

Keep vein open (KVO) infusion flow control devices are provided. The KVO infusion flow control device couples to intravenous (IV) tubing and includes a flow controller that provides a full open fluid flow rate through an outlet portion of the IV tubing when the flow controller is in an open position, and a KVO fluid flow rate through the outlet portion of the IV tubing when the flow controller is in a KVO position. Visual indicators are disposed on the KVO infusion flow control device.

20 Claims, 22 Drawing Sheets

(51) Int. Cl.
  *A61M 39/10* (2006.01)
  *A61M 39/28* (2006.01)
  *A61M 5/31* (2006.01)

(52) U.S. Cl.
  CPC .......... *A61M 39/10* (2013.01); *A61M 39/285* (2013.01); *A61M 2005/14208* (2013.01); *A61M 2005/3125* (2013.01); *A61M 2039/1083* (2013.01); *A61M 2039/1088* (2013.01)

(58) Field of Classification Search
  CPC .............. A61M 5/168; A61M 5/16804; A61M 5/16877; A61M 2005/1401; A61M 39/22; A61M 2039/229
  See application file for complete search history.

(56) References Cited

U.S. PATENT DOCUMENTS

| | | | |
|---|---|---|---|
| 6,500,156 B1 * | 12/2002 | Stansbury | A61M 5/1424 604/257 |
| 7,491,191 B2 | 2/2009 | Wagner et al. | |
| 2010/0154909 A1 | 6/2010 | Oh et al. | |
| 2013/0023792 A1 * | 1/2013 | Markey | A61B 5/150992 600/578 |
| 2014/0066893 A1 | 3/2014 | Valentini | |
| 2019/0125235 A1 * | 5/2019 | Hoan | A61M 39/223 |

FOREIGN PATENT DOCUMENTS

| | | |
|---|---|---|
| WO | WO-8809893 A1 | 12/1988 |
| WO | WO-9325269 A1 | 12/1993 |
| WO | WO-2013013129 A1 | 1/2013 |

OTHER PUBLICATIONS

Invitation to Pay Additional Fees for International Patent Application No. PCT/US2021/029465, dated Aug. 12, 2021, 14 pages.
Japanese Office Action for Application No. 2022-566133, dated Dec. 3, 2024, 4 pages including translation.

* cited by examiner

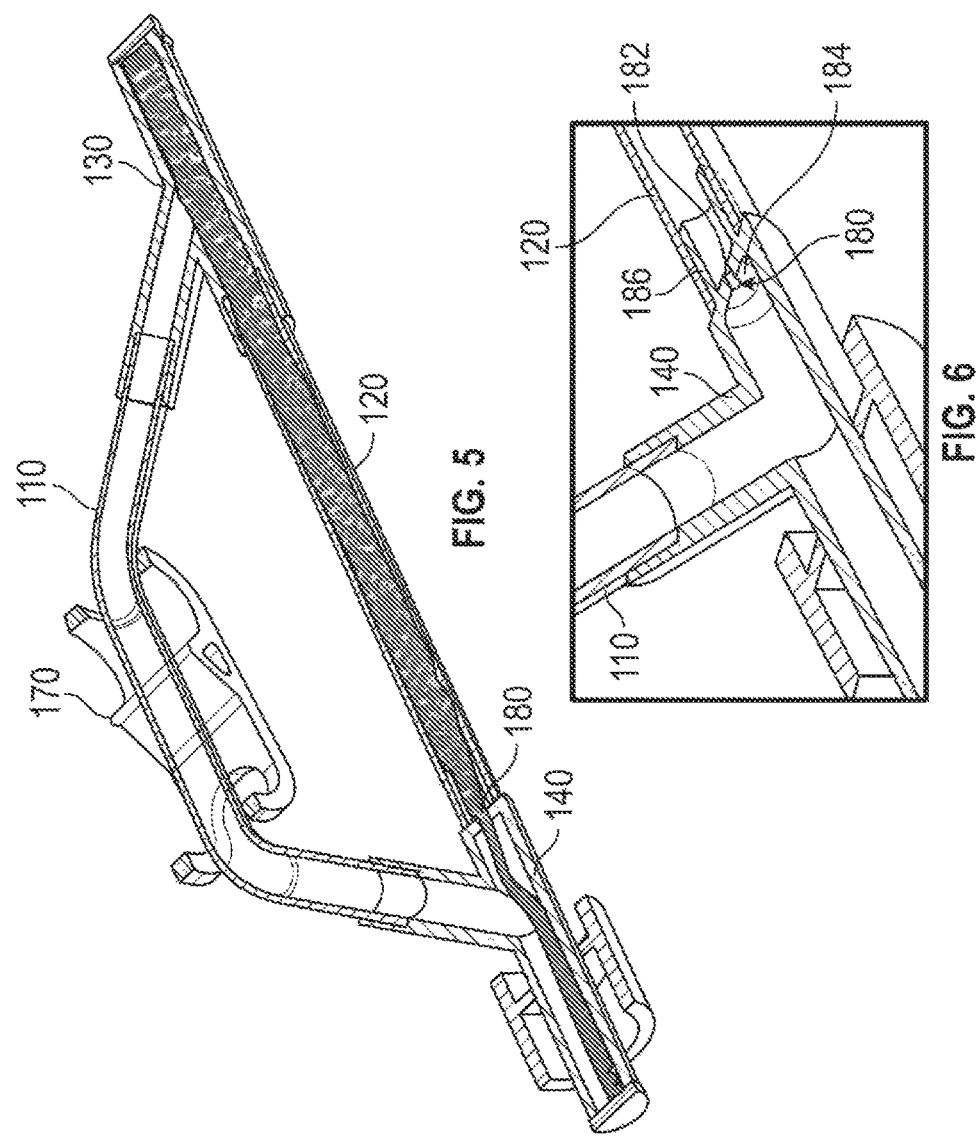
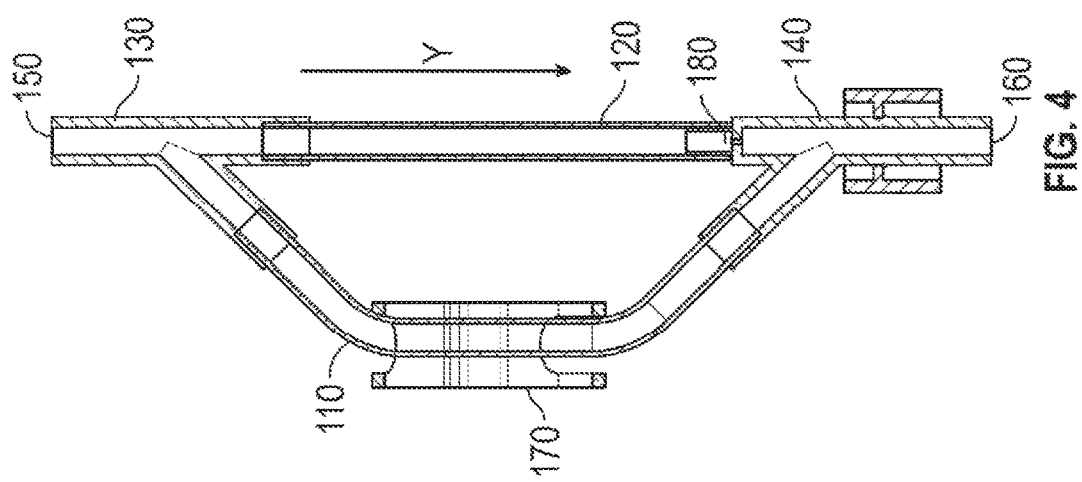

KEEP VEIN OPEN INFUSION FLOW CONTROL DEVICE

CROSS-REFERENCES TO RELATED APPLICATIONS

This application is a continuation of U.S. patent application Ser. No. 16/862,308, entitled "KEEP VEIN OPEN INFUSION FLOW CONTROL DEVICE," filed Apr. 29, 2020, now U.S. Pat. No. 11,400,210 issued on Aug. 2, 2022, the disclosure of which is hereby incorporated by reference in its entirety for all purposes.

BACKGROUND

During use of an intravenous (IV) infusion set, occlusion in the IV line is a common but undesirable occurrence to the patient's IV access because of the clotting function of blood fibrin. The causes of catheter occlusion might be thrombotic, related to drug or parenteral nutrition precipitates or mechanical. Occlusion due to this effect also provide potential nesting material for microorganisms and thus also increase the risk of catheter-related bloodstream infection. Typical solutions to catheter occlusion are flushing and locking methods, such as tissue plasminogen activator (tPA), Heparin locks and catheter replacements. However, these typical flushing and locking methods have a significant impact on clinician time and in-patient costs.

It is desirable to provide keep vein open (KVO), also known as to keep open (TKO), infusion flow control devices having safe, consistent fluid flow control that can be easily set to keep fluid flow in the IV line at a KVO rate, thus reducing clinician time and in-patient costs.

SUMMARY

The present disclosure provides keep vein open infusion flow control devices to rapidly and easily set gravity IV infusion rates to KVO without interaction with other IV infusion set components.

In one or more embodiments, a KVO infusion flow control device is provided. The KVO infusion flow control device includes an inlet tube connector comprising an IV inlet port, a first outlet port and a second outlet port. The KVO infusion flow control device also includes an outlet tube connector comprising an IV outlet port, a first inlet port, a second inlet port and a flow control orifice disposed within the second inlet port. The KVO infusion flow control device further includes a full flow tube coupled at one end to the first outlet port of the inlet tube connector and coupled at another end to the first inlet port of the outlet tube connector. The KVO infusion flow control device also includes a KVO flow tube coupled at one end to the second outlet port of the inlet tube connector and coupled at another end to the second inlet port of the outlet tube connector. The KVO infusion flow control device further includes a single flow controller coupled to the full flow tube, the flow controller configured to control fluid flow through the full flow tube, wherein the KVO flow tube is configured to always provide some fluid flow.

In one or more aspects, the flow controller is configured to provide full fluid flow through the full flow tube into the outlet tube connector when the flow controller is disposed in a first position that does not occlude the full flow tube. In one or more aspects, the flow controller is configured to shut off fluid flow through the full flow tube into the outlet tube connector when the flow controller is disposed in a second position that occludes the full flow tube to a predetermined degree. In one or more aspects, the flow control orifice is configured to limit fluid flow into the outlet tube connector when the flow controller is disposed in the second position. In one or more aspects, the flow control orifice is sized and shaped to provide a predetermined KVO fluid flow rate into the outlet tube connector when the flow controller is disposed in the second position. In one or more aspects, an inlet connector is coupled to the IV inlet port, the inlet connector configured to be coupled to an inlet IV tube.

In one or more aspects, an outlet connector is coupled to the IV outlet port, the outlet connector configured to be coupled to an outlet IV tube. In one or more aspects, the flow control orifice comprises a tube engagement portion disposed within an internal diameter of the KVO flow tube. In one or more aspects, the flow control orifice further comprises a restriction portion disposed adjacent to the tube engagement portion, the restriction portion configured to block fluid flow from the tube engagement portion into the outlet connector. In one or more aspects, the flow control orifice further comprises a flow portion disposed within the restriction portion, the flow portion configured to restrict fluid flow into the outlet connector to a KVO fluid flow rate. In one or more aspects, the flow controller is a pinch clamp.

In one or more embodiments, a KVO infusion flow control device is provided. The KVO infusion flow control device includes a body comprising a full open orifice disposed through the body and a separate KVO orifice disposed through the body at an angle to the full open orifice, a control member coupled to the body and a visual indicator. A first position of the control member is configured to engage the full open orifice with a fluid flow path to provide full fluid flow through an intravenous (IV) tube and a second position of the control member is configured to engage the KVO orifice with the fluid flow path to provide KVO fluid flow through the IV tube.

In one or more aspects, the control member includes an open control arm having a first visual indicator disposed thereon, the open control arm parallel to the full open orifice, and a KVO control arm having a second visual indicator disposed thereon, the KVO control arm parallel to the KVO orifice, wherein the body is rotatably coupled to a fluid flow housing, the fluid flow housing including an inlet connector configured to receive a fluid inlet IV tube at one end of the fluid flow housing and an outlet connector configured to receive a fluid outlet IV tube at an opposing end of the fluid flow housing.

In one or more aspects, a first flange is disposed circumferentially around a portion of the inlet connector and a second flange is disposed circumferentially around a portion of the outlet connector, wherein the fluid inlet IV tube is received in a gap between the first flange and the inlet connector and the fluid outlet IV tube is received in a gap between the second flange and the outlet connector.

In one or more aspects, the control member includes a circular control switch having a first visual indicator disposed on a top surface, a gripping extension disposed on the top surface, the gripping extension parallel to the KVO orifice and a second visual indicator disposed on a top surface of the gripping extension, wherein the body is rotatably coupled to a fluid flow housing, the fluid flow housing configured to receive a fluid inlet IV tube at one end of the fluid flow housing and to receive a fluid outlet IV tube at an opposing end of the fluid flow housing.

In one or more embodiments, a KVO infusion flow control device is provided. The KVO infusion flow control device includes a body, a switch movably coupled to the body between a full open flow position and a separate KVO flow position and a visual indicator. A first position of the switch is configured to engage a full open orifice with a fluid flow path to provide full fluid flow through intravenous (IV) tubing and a second position of the switch is configured to engage a KVO orifice with the fluid flow path to provide KVO fluid flow through the IV tubing.

In one or more aspects, the switch comprises a slide switch disposed within a switch channel in the body, wherein the IV tubing comprises a fluid inlet IV tube and a fluid outlet IV tube, wherein the body is configured to receive the fluid inlet IV tube at a first connector disposed on a side wall of the body and to receive the fluid outlet IV tube at a second connector disposed on an opposing side wall of the body, wherein a full open channel is disposed through a width of the slide switch and is aligned with the first and second connectors in the first position, and wherein a KVO channel is disposed through the width of the slide switch and is aligned with the first and second connectors in the second position.

In one or more aspects, the switch comprises a rocker switch pivotably disposed in a tube channel of the body, wherein a first portion of the rocker switch is an open engagement member sized and shaped to engage the IV tubing such that the IV tubing is not occluded when the rocker switch is in the first position, and wherein a second portion of the rocker switch is a KVO engagement member sized and shaped to engage the IV tubing such that the IV tubing is occluded when the rocker switch is in the second position.

In one or more aspects, the switch comprises a rocker switch pivotably disposed in a switch channel of the body, wherein an engagement surface of the rocker switch does not occlude the IV tubing when the rocker switch is in the first position, and wherein a retaining clip is disposed on the body, the retaining clip configured to hold an engagement member the rocker switch so that the IV tubing is occluded by the engagement surface when the rocker switch is in the second position.

In one or more aspects, the switch is slidably coupled to the body, the switch including a leading portion disposed within the body, an exterior surface disposed within the body, a switch rib and a switch connector configured to receive an inlet IV tube, and the body including a body connector configured to receive an outlet IV tube, a valve disposed adjacent to the body connector, the valve having pivotably connected valve flaps, a seal disposed on a portion of the exterior surface of the switch and a gripper, wherein the gripper of the body retains the switch rib and the leading portion of the switch holds the valve flaps in the full open flow position when the switch is in the first position, and wherein the leading portion of the switch is removed from engagement with the valve flaps and the valve flaps are biased in a closed position having a KVO gap when the switch is in the second position.

Additional features and advantages of the disclosure will be set forth in the description below and, in part, will be apparent from the description or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

FIG. 4 is a top view of the KVO infusion fluid flow control device of FIG. 1 showing the fluid flow path with the pinch clamp closed, according to some aspects of the disclosure.

FIG. 5 is a cross-sectional perspective view of the KVO infusion fluid flow control device of FIG. 4, according to some aspects of the disclosure FIG. 6 is an enlarged partial view of the KVO infusion fluid flow control device of FIG. 5, according to some aspects of the disclosure.

DETAILED DESCRIPTION

Figure 1:
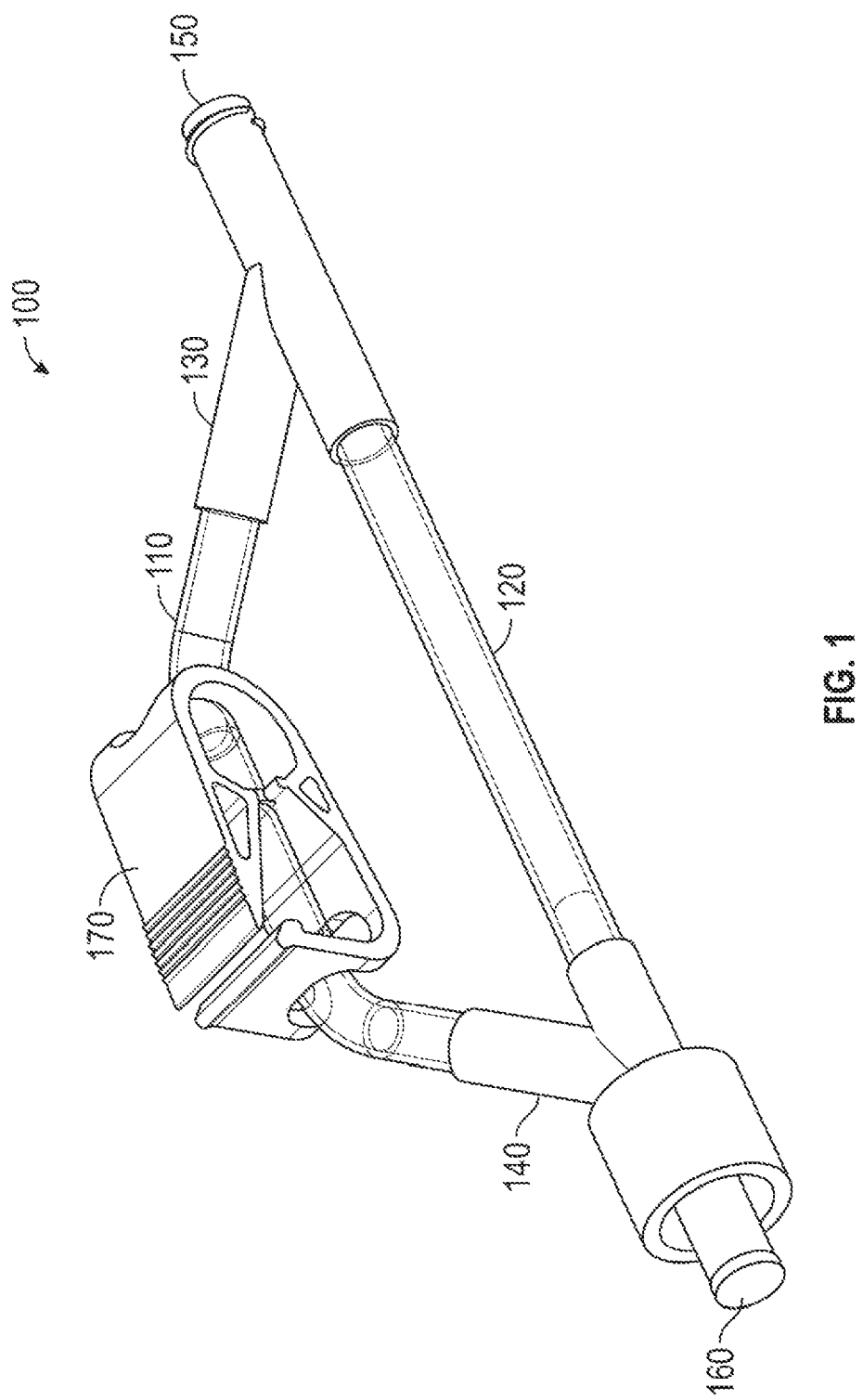
FIG. 1 is a perspective view of an example KVO infusion fluid flow control device, according to some aspects of the disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Typical connectors and flow regulators for gravity IV infusion sets do not have a way of setting a specific KVO rate. While medical infusion pumps may have KVO rate setting features, KVO features are not typically found on current gravity IV infusion sets.

According to some aspects of the disclosure, a KVO infusion flow control device allows a clinician (e.g., health care provider) to rapidly and easily set gravity IV infusion rates to a KVO rate without interaction with other components in the IV infusion set (e.g., catheter, flush syringe, injection port, IV-line component, roller clamp, flow controller). This frees the clinician to perform other duties worry free as the KVO infusion flow control device keeps the injection site operational while maintaining the KVO rate.

According to some aspects of the disclosure, the KVO infusion flow control device reduces occlusion in the catheter and keeps the IV line open for future use. According to some aspects of the disclosure, the KVO infusion flow control device reduces the probabilities that blood clots and drug precipitates will form, thus keeping the IV site (e.g., injection site of needle in vein) operational over time. According to some aspects of the disclosure, the KVO infusion flow control device reduces connections necessary to maintain the IV site (e.g flush syringe), thus keeping the IV site operational over time and reducing exposure to contaminants and infectious agents that could potentially enter the patient's bloodstream. According to some aspects of the disclosure, the KVO infusion flow control device reduces blood reflux occurrence due to a continual flow of IV fluid.

A KVO infusion flow control device 100 is shown in FIGS. 1-9, according to some aspects of the disclosure. The KVO infusion flow control device 100 includes a full flow tube 110 and a KVO flow tube 120 that are each coupled to an inlet tube connector 130 (e.g., Y-connector) at one end and an outlet tube connector 140 (e.g., Y-connector) at the other end. The inlet tube connector 130 includes an IV inlet port 132, a first outlet port 134 and a second outlet port 136. The outlet tube connector 140 includes an IV outlet port 142, a first inlet port 144 and a second inlet port 146. The IV inlet port 132 is coupled to an inlet connector 150 (e.g., female Luer connector) and the IV outlet port 142 is coupled to an outlet connector 160 (e.g., male Luer connector). A flow controller 170 (e.g., pinch clamp) is coupled to the full flow tube 110 to provide control of the fluid flow through the full flow tube 110. For example, when the flow controller 170 is in an open position, the fluid may have a fully open flow in the full flow tube 110, whereas when the flow controller 170 is in a closed position, fluid flow may be completely blocked in the full flow tube 110. A flow control orifice 180 (see FIGS. 2-6) is disposed within the second inlet port 146 and the flow control orifice 180 is sized and shaped to provide a desired KVO fluid flow rate.

Figure 3:
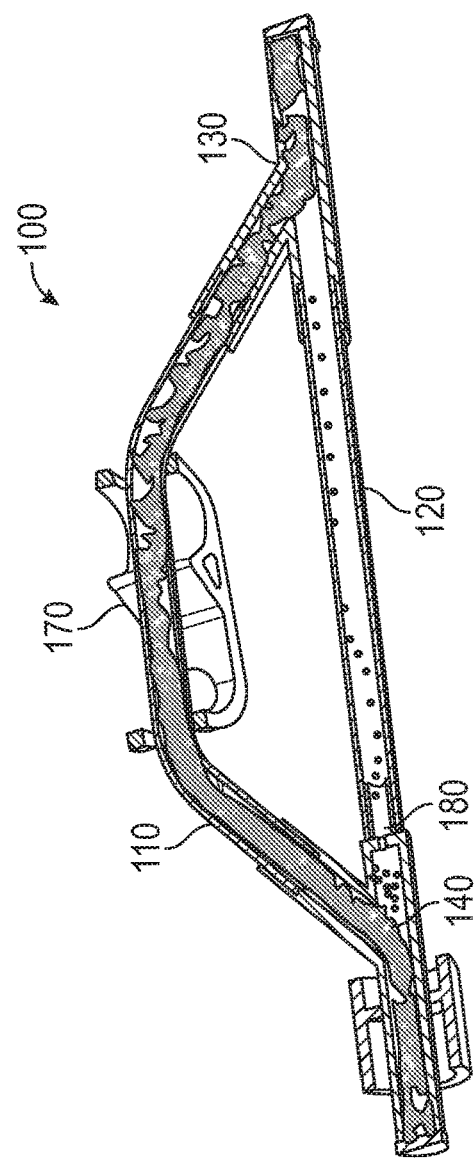
FIG. 3 is a cross-sectional perspective view of the KVO infusion fluid flow control device of FIG. 2, according to some aspects of the disclosure.
Figure 2:
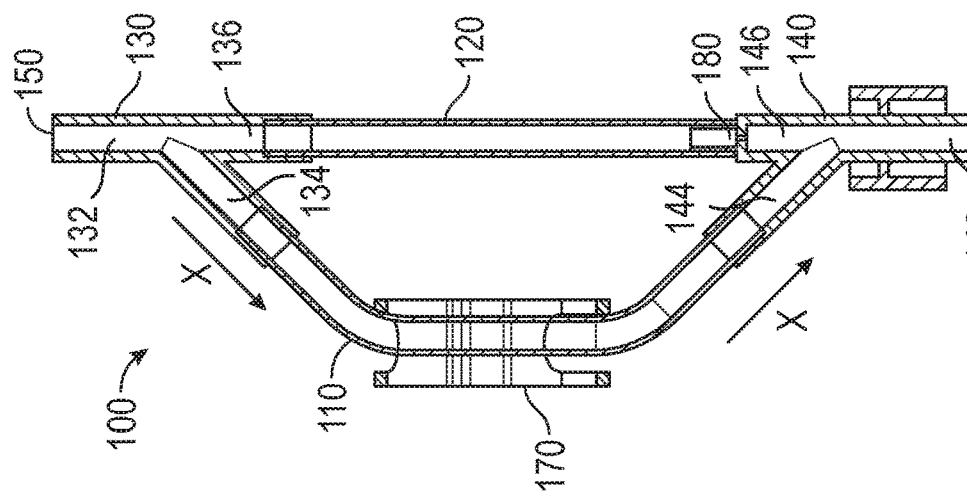
FIG. 2 is a top view of the KVO infusion fluid flow control device of FIG. 1 showing the fluid flow path with the pinch clamp open, according to some aspects of the disclosure.

As shown in FIGS. 2 and 3, with the flow controller 170 in an open flow setting, the majority of the fluid flowing into the inlet tube connector 130 takes the path of least resistance and flows out the first outlet port 134 and through the full flow tube 110 along the open flow path X, according to some aspects of the disclosure. Here, some portion of fluid may still flow out the second outlet port 136 and through the KVO flow tube 120, but the fluid flow is restricted by the flow control orifice 180 such that the fluid backs up into the inlet tube connector 130. This causes additional fluid coming into the inlet tube connector 130 from a fluid source (e.g., fluid bag, needless syringe) to divert into the full flow tube 110 and flow freely without restriction to the first inlet port 144 and to exit the IV outlet port 142 at a fully open flow rate.

As shown in FIGS. 4 and 5, with the flow controller 170 in a flow off setting, the majority of the fluid flowing into the inlet tube connector 130 takes the path of least resistance and flows out the second outlet port 136 and through the KVO flow tube 120 along the open flow path Y, according to some aspects of the disclosure. Here, a portion of fluid remains in the full flow tube 110 from the flow controller 170 to the inlet tube connector 130. This causes additional fluid coming into the inlet tube connector 130 from the fluid source (not shown) to divert into the KVO flow tube 120 and flow freely through the KVO flow tube 120 to the second inlet port 146 until being restricted by the flow control orifice 180 in the outlet tube connector 140. The fluid then exits the IV outlet port 142 at a KVO flow rate.

As shown in FIG. 6, according to some aspects of the disclosure, the flow control orifice 180 may have a flow portion 182, a restriction portion 184 and a tube engagement portion 186. The engagement portion is configured to engage or couple with the KVO flow tube 120. The engagement portion 186 has a narrower internal diameter/volume than the KVO flow tube 120, which provides for a first restriction in the fluid flow into the outlet tube connector 140. The restriction portion 184 is configured to block the flow of fluid from the KVO flow tube 120 into the outlet tube connector 140 through the area covered by the restriction portion 184. The flow portion 182 is a smaller opening (e.g., circular hole) disposed within the restriction portion 184 and configured to restrict fluid flow to a lower flow rate (e.g., KVO flow rate) than the fully open flow rate through the KVO flow tube 120 and the first restricted flow rate through the engagement portion 186.

Thus, the size and shape of the flow portion 182 dictates the final flow rate of the fluid into the outlet tube connector 140. For example, a neonatal gravity IV set for use with an infant may have a KVO infusion flow control device 100 with a very small flow portion 182, thus causing a low KVO fluid flow rate that is appropriate for a small vein and/or body size. As another example, a gravity IV set for large adults may have a KVO infusion flow control device 100 with a larger flow portion 182, resulting in a higher KVO fluid flow rate that is appropriate for a larger vein and/or body size. The flow portion 182 may be configured as any shape (e.g., circle, square, oval, triangle), where different shapes may provide different flow rates and fluid turbulence levels.

Figure 8:
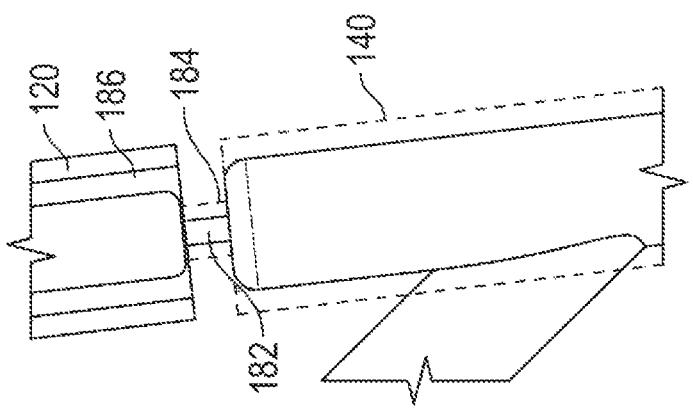
FIG. 8 is an enlarged partial view of the fluid volume of FIG. 7, according to some aspects of the disclosure.
Figure 7:
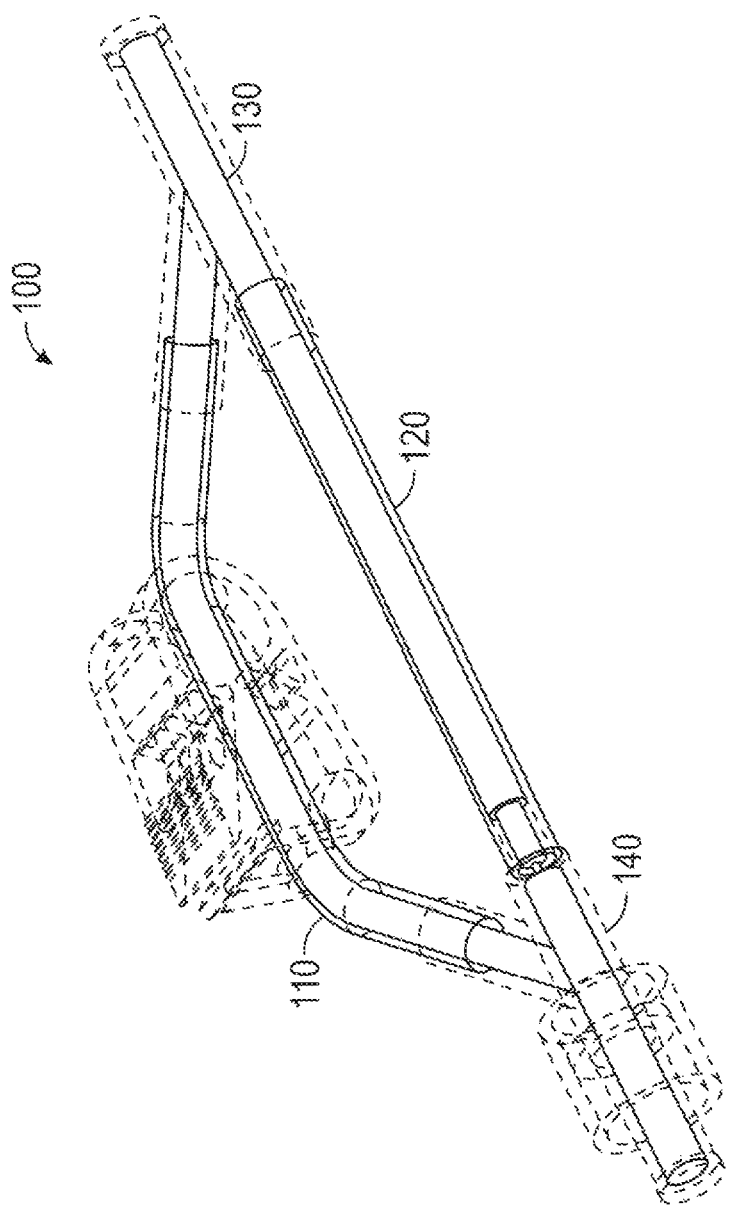
FIG. 7 is a schematic view of the fluid volume throughout the KVO infusion fluid flow control device of FIG. 1 for both all states, according to some aspects of the disclosure.

FIGS. 7 and 8 are schematic views depicting the available interior volume for fluid flow throughout the KVO infusion flow control device 100. The smaller available fluid volume in the engagement portion 186 provides for a somewhat restricted flow rate through the engagement portion 186. The much smaller available fluid volume in the flow portion 182 provides for a more restricted flow rate (e.g., KVO flow rate) through the flow portion 182. Accordingly, the fluid flow output from the flow control orifice 180 into the outlet tube connector 140 is controlled at the KVO flow rate.

Figure 9:
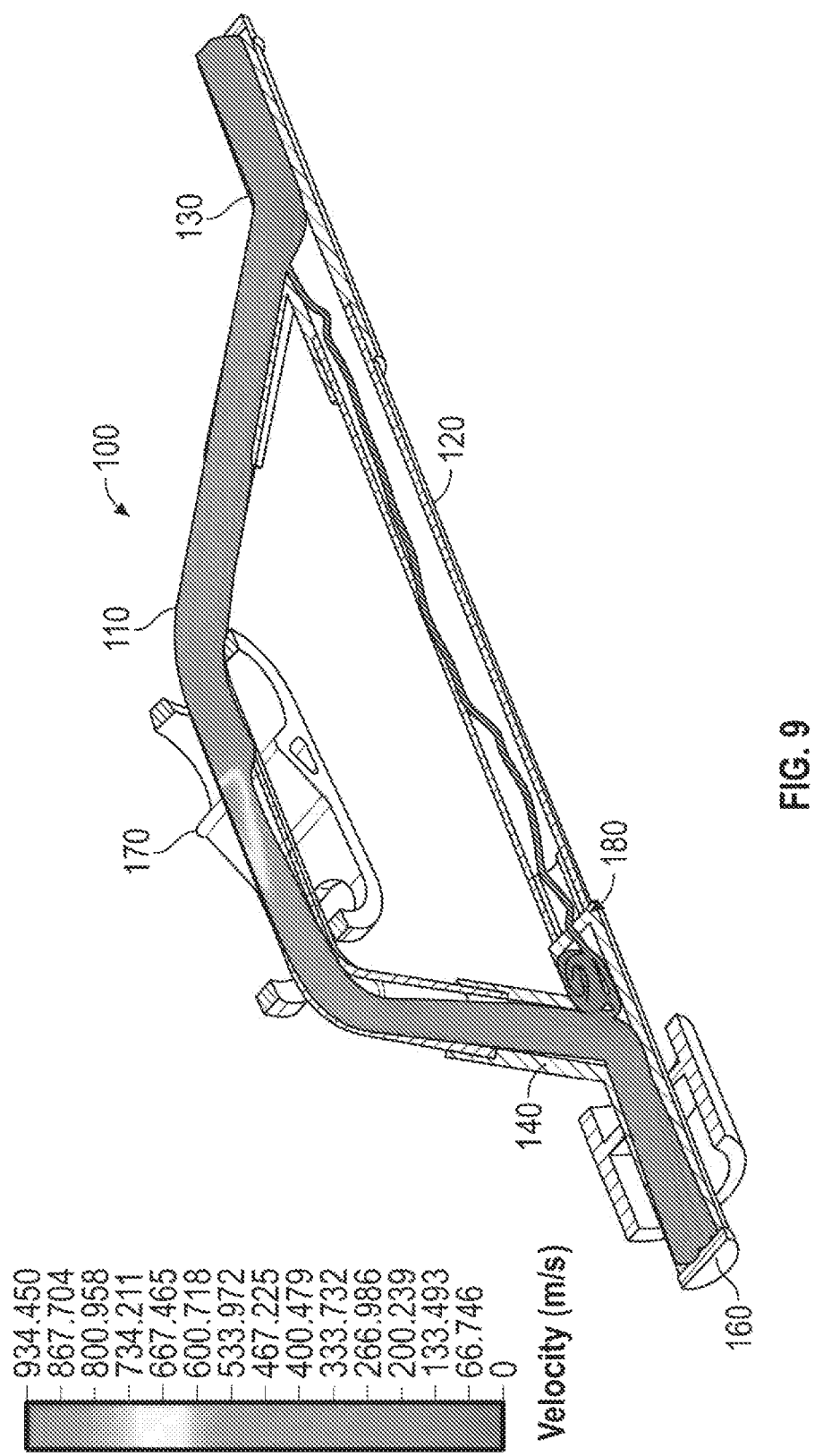
FIG. 9 is a schematic view of a fluid flow velocity model of the KVO infusion fluid flow control device of FIG. 2, according to some aspects of the disclosure.
Figure 10A:
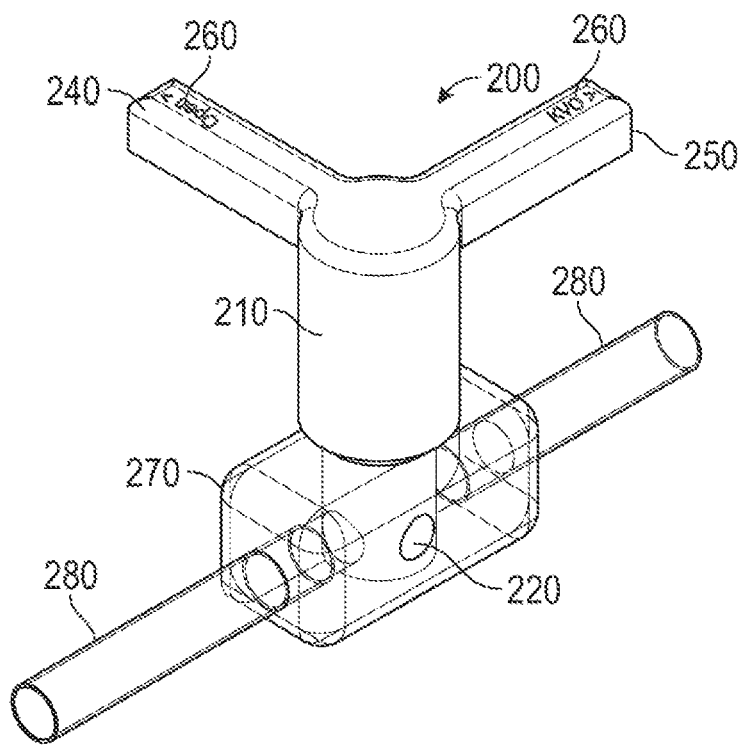
FIGS. 10A-10E are various views of a KVO infusion fluid flow control device, according to some aspects of the disclosure.
Figure 10B:
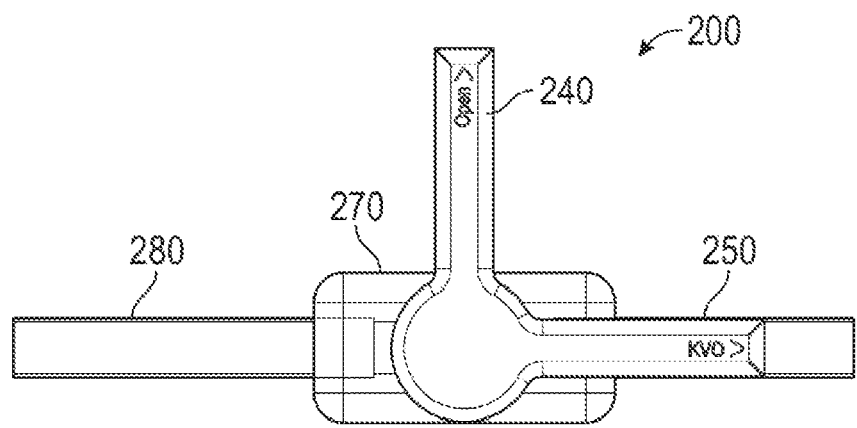
Figure 10C:
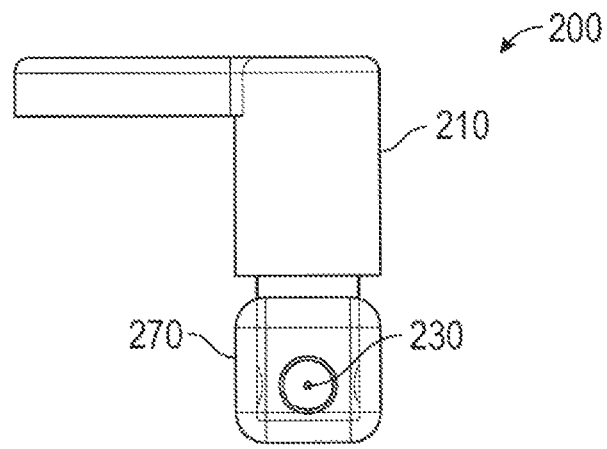
Figure 10D:
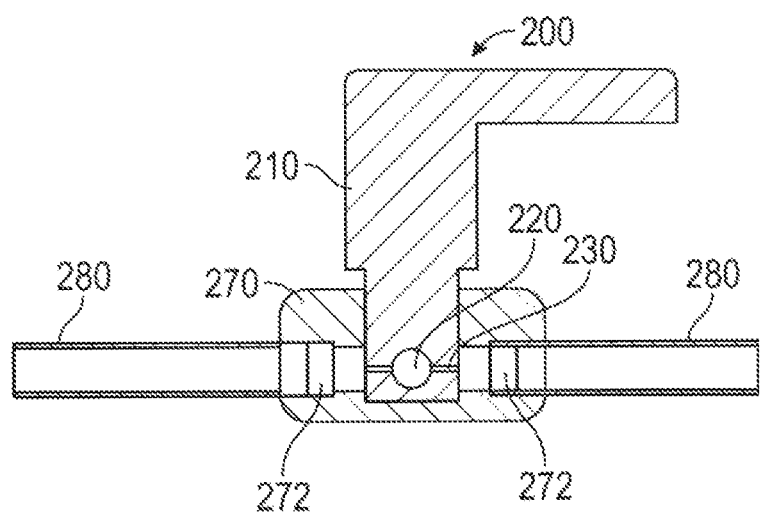
Figure 10E:
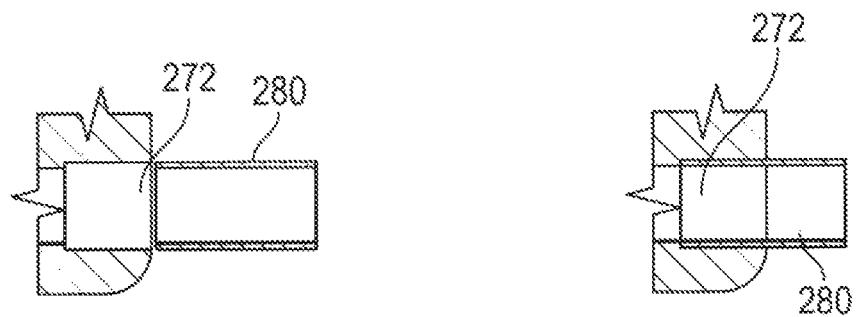
Figure 11A:
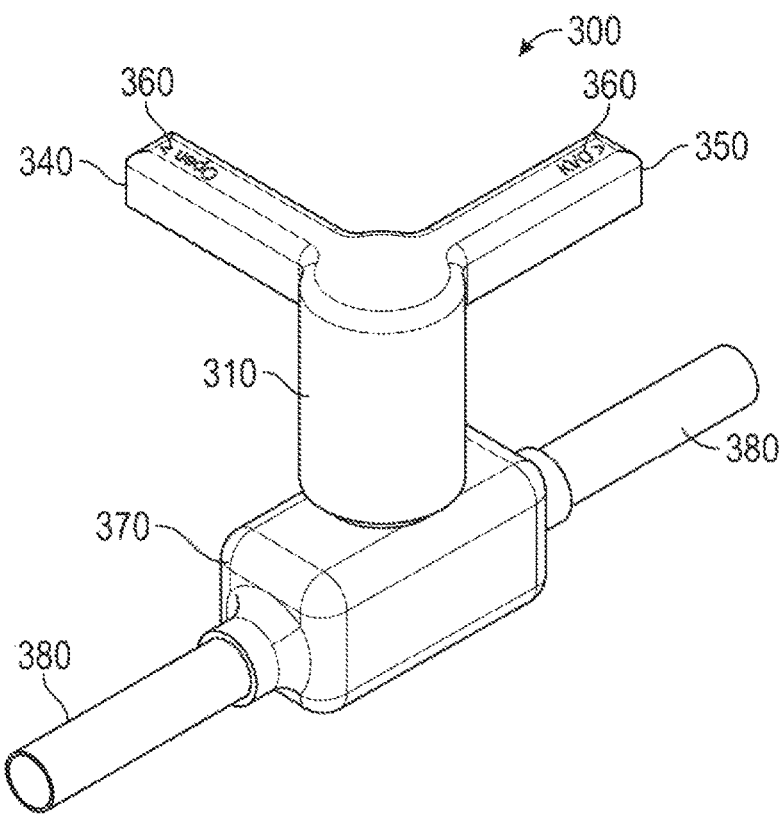
FIGS. 11A-11D are various views of a KVO infusion fluid flow control device, according to some aspects of the disclosure.
Figure 11B:
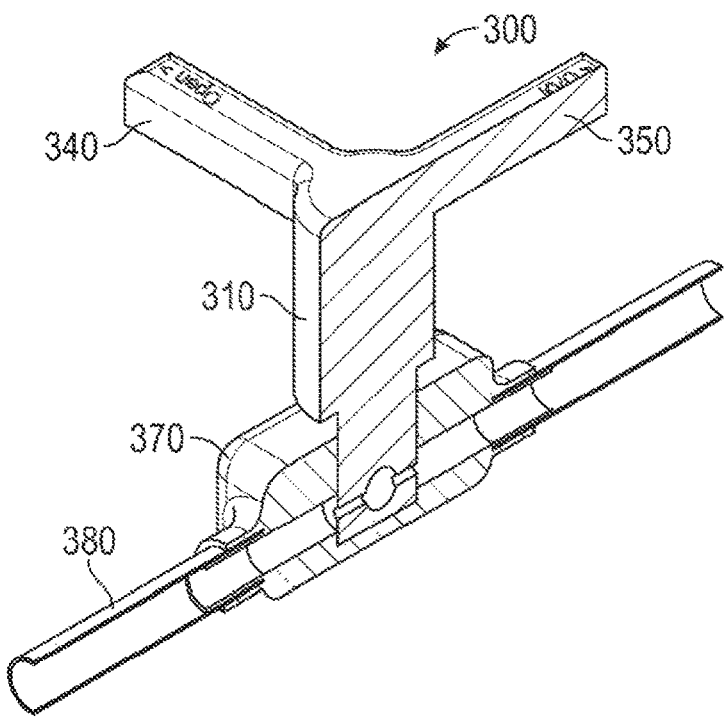
Figure 11C:
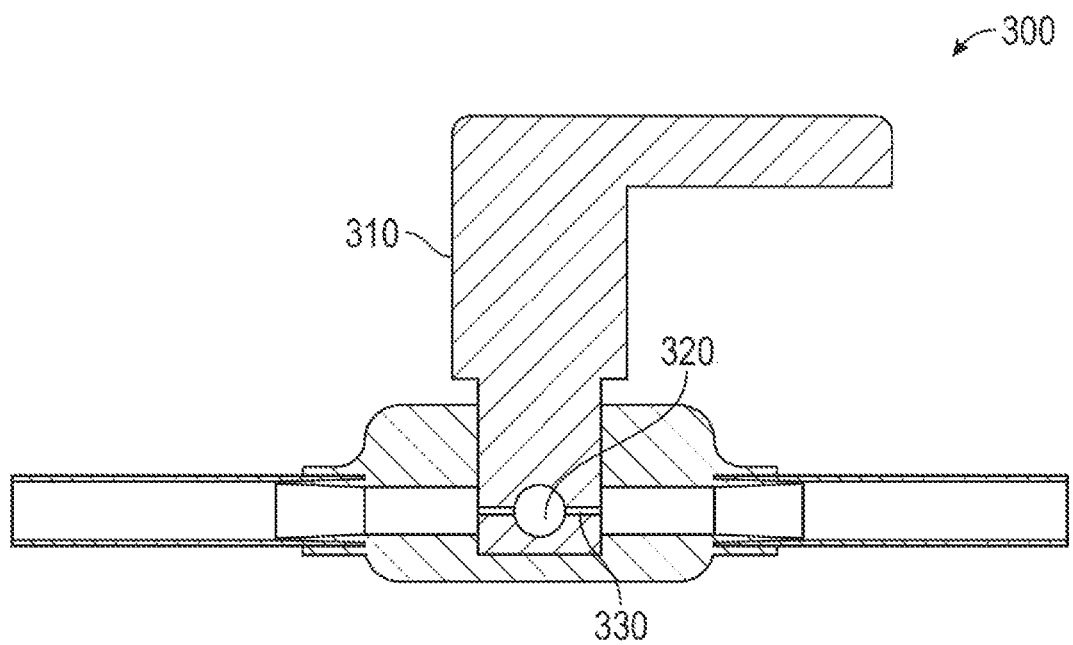
Figure 11D:
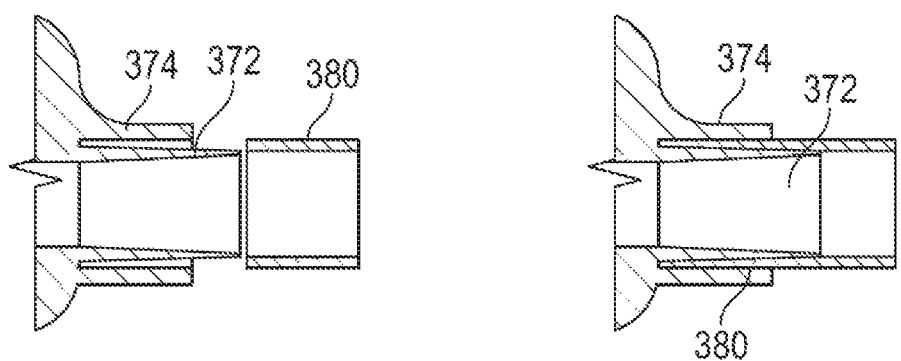
Figure 12A:
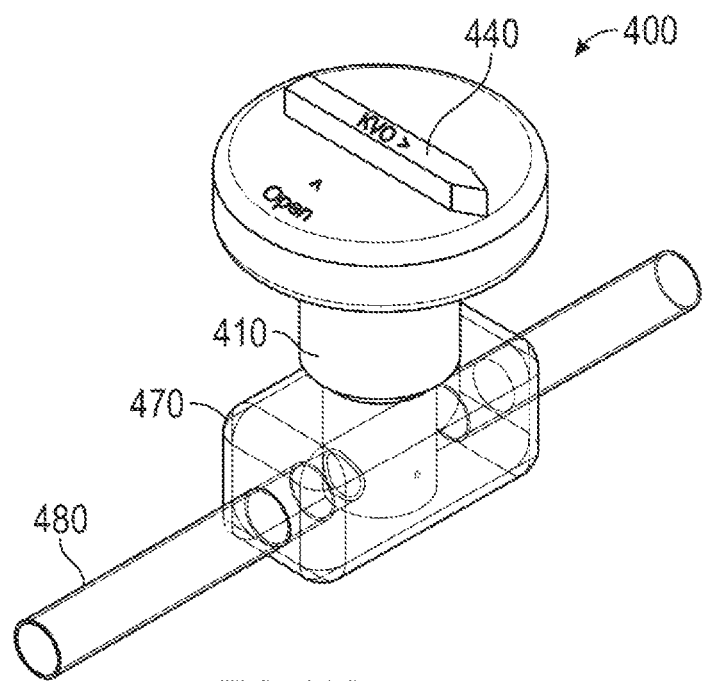
FIGS. 12A-12D are various views of a KVO infusion fluid flow control device, according to some aspects of the disclosure.
Figure 12B:
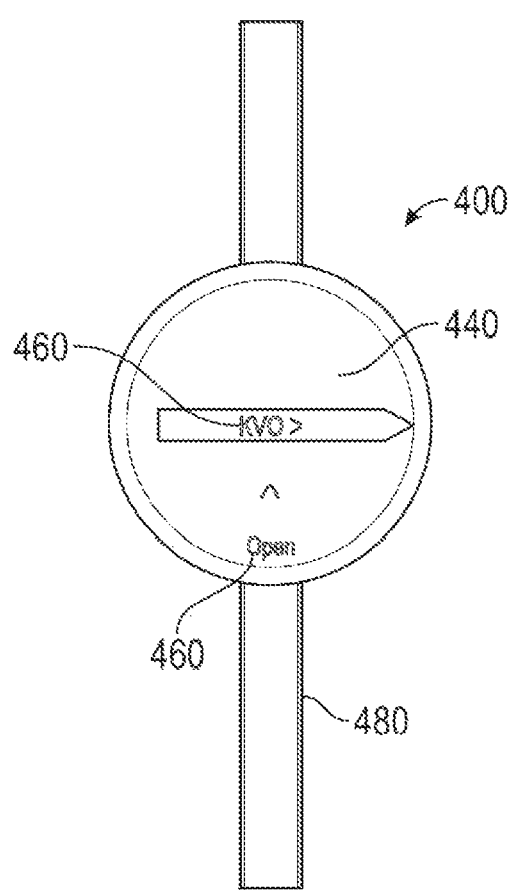
Figure 12C:
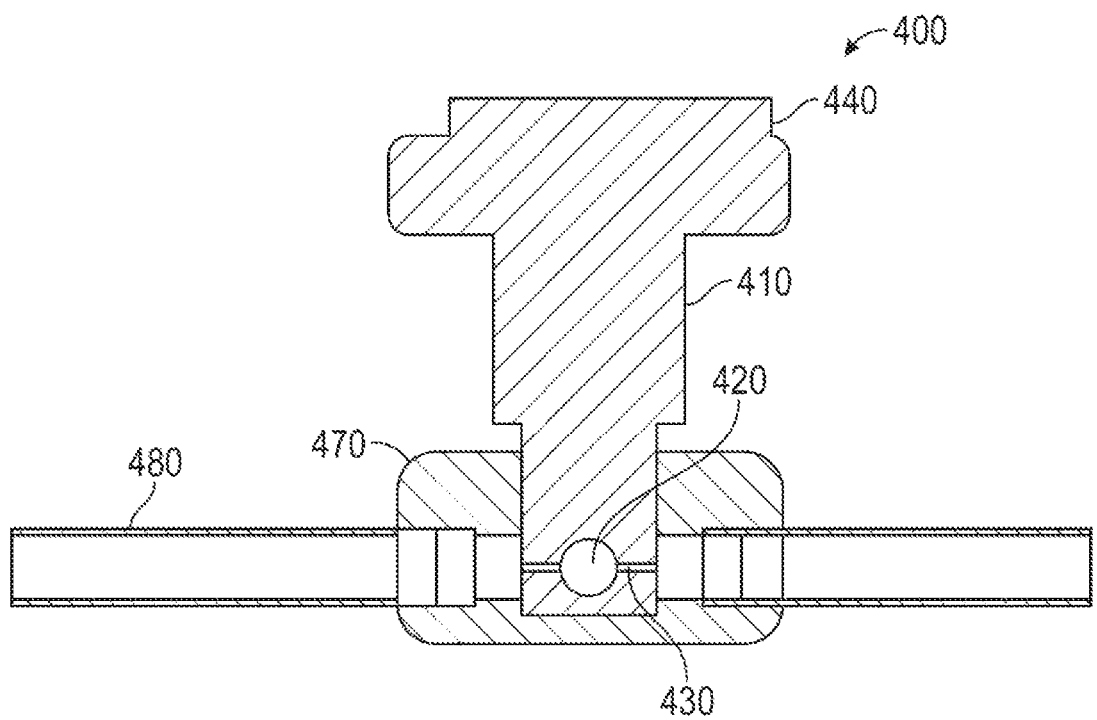
Figure 12D:
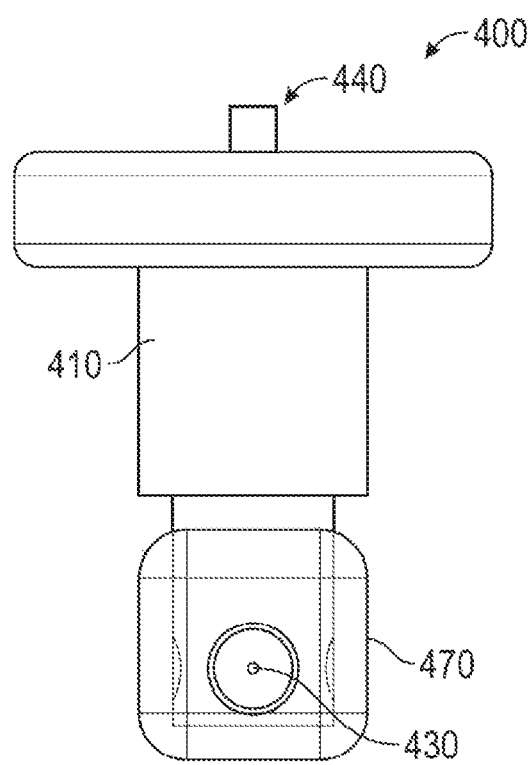
Figure 13A:
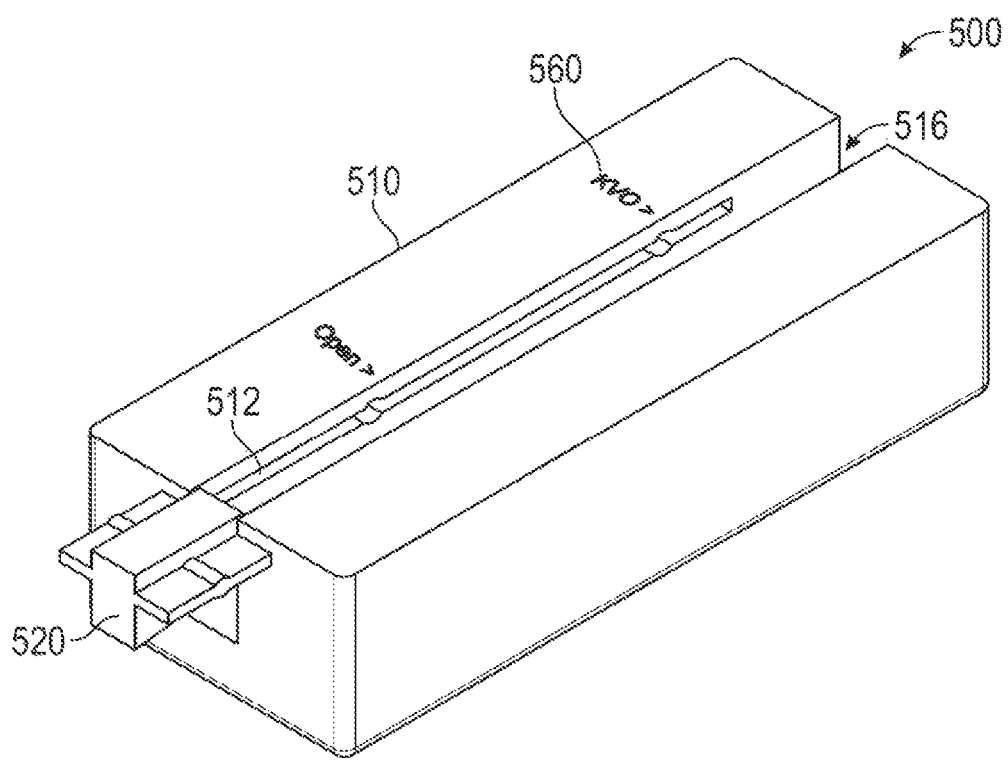
FIGS. 13A-13G are various views of a KVO infusion fluid flow control device, according to some aspects of the disclosure.
Figure 13B:
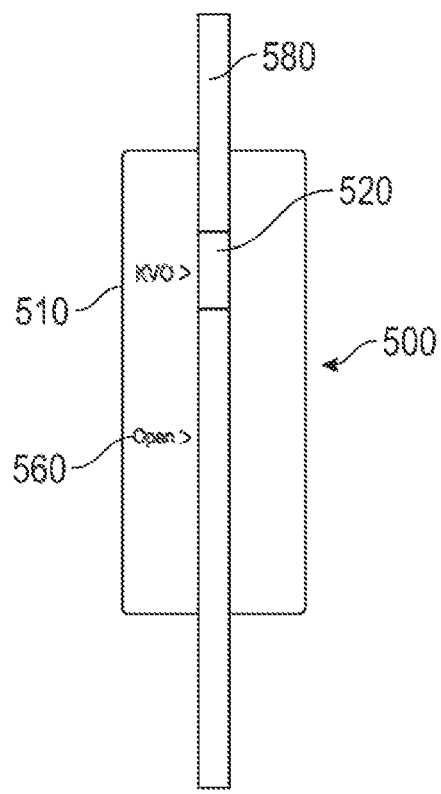
Figure 13C:
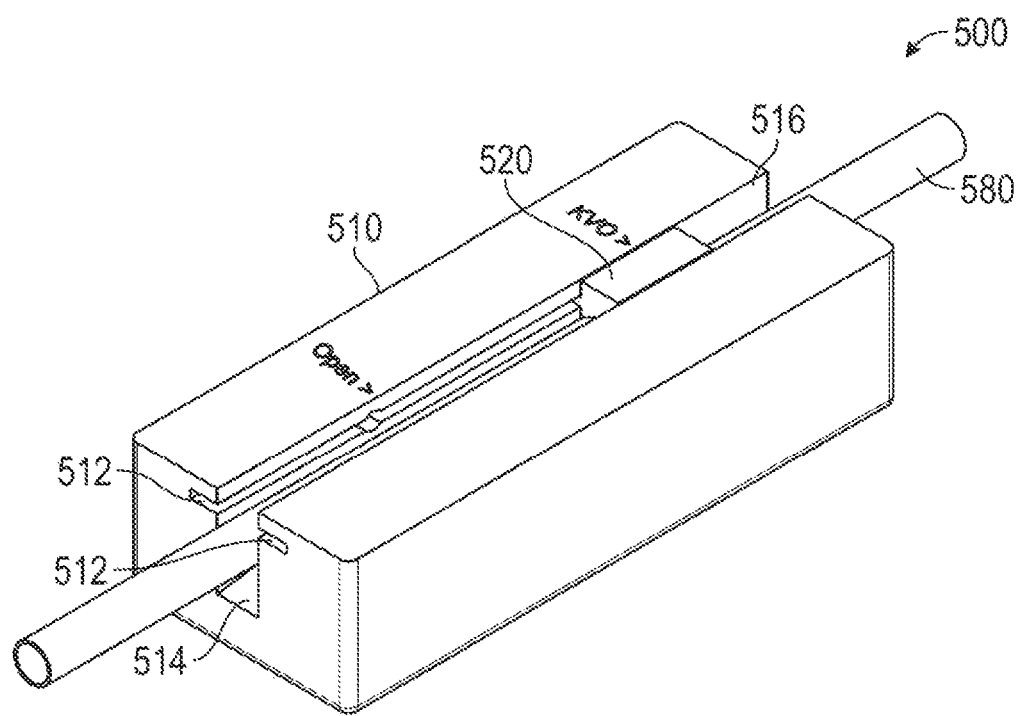
Figure 13D:
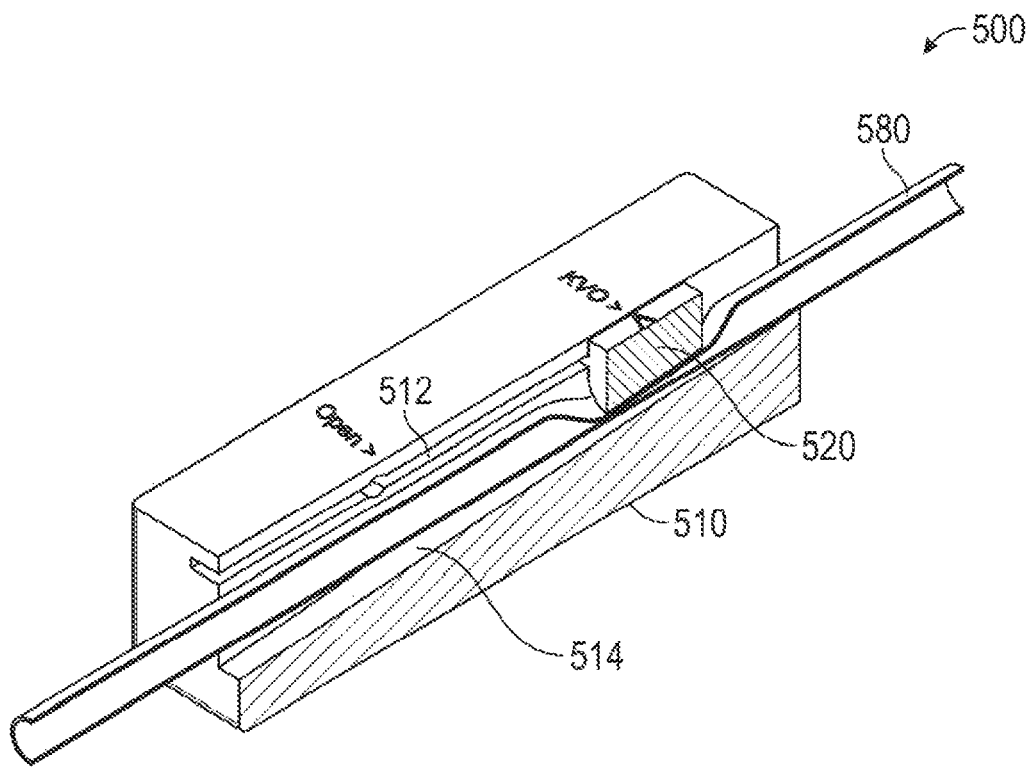
Figure 13E:
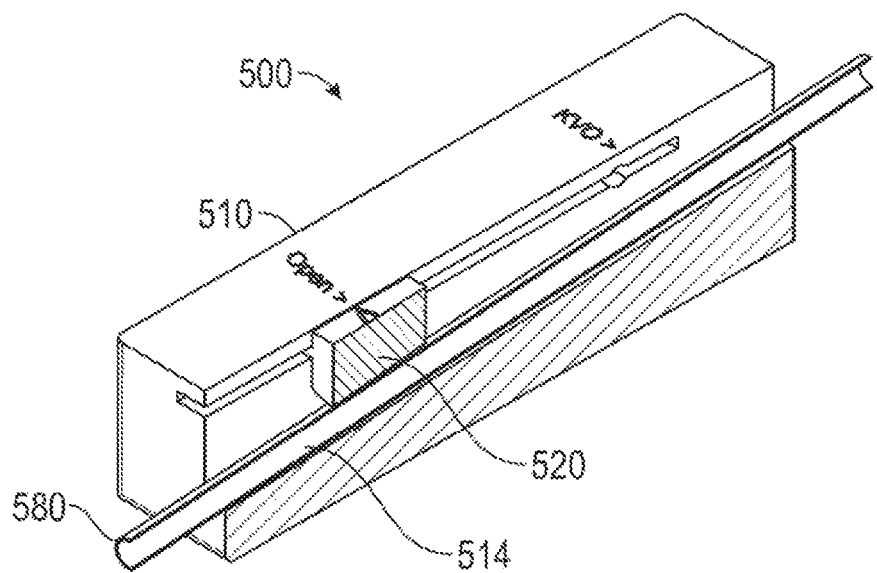
Figure 13F:
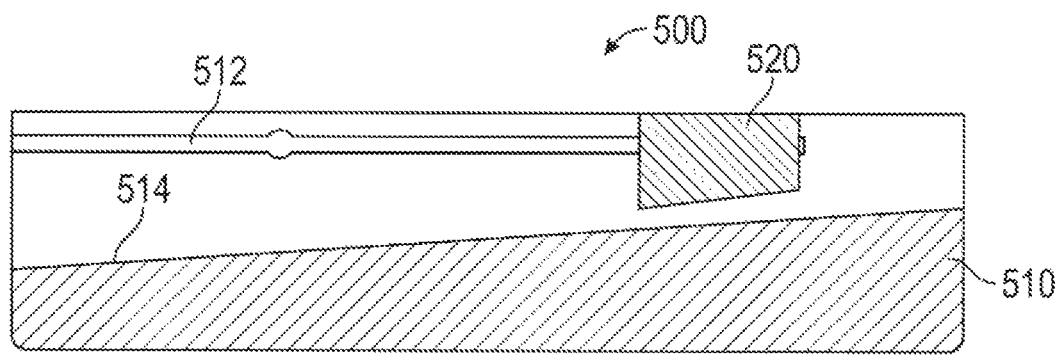
Figure 13G:
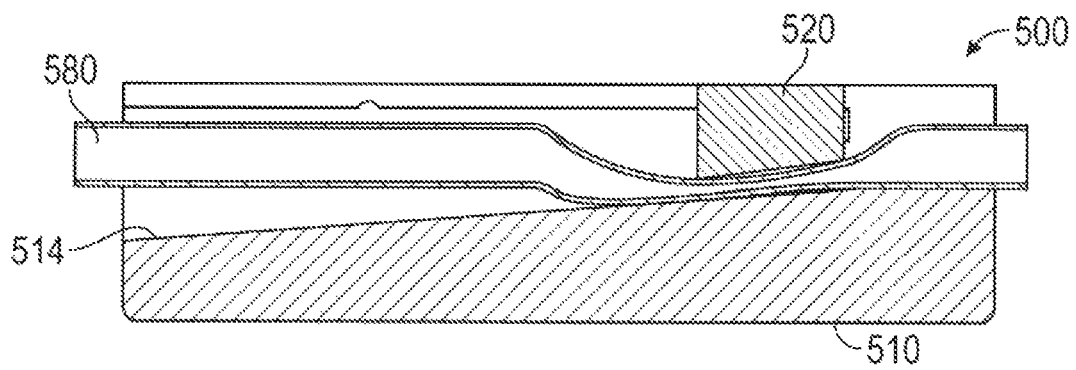
Figure 14C:
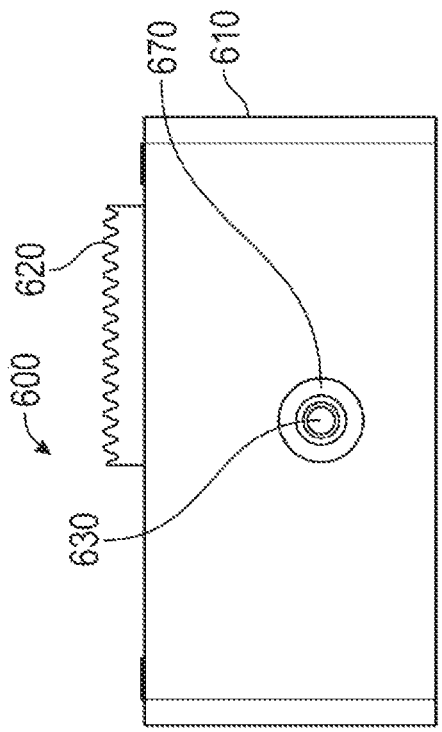
FIGS. 14A-14D are various views of a KVO infusion fluid flow control device, according to some aspects of the disclosure.
Figure 14D:
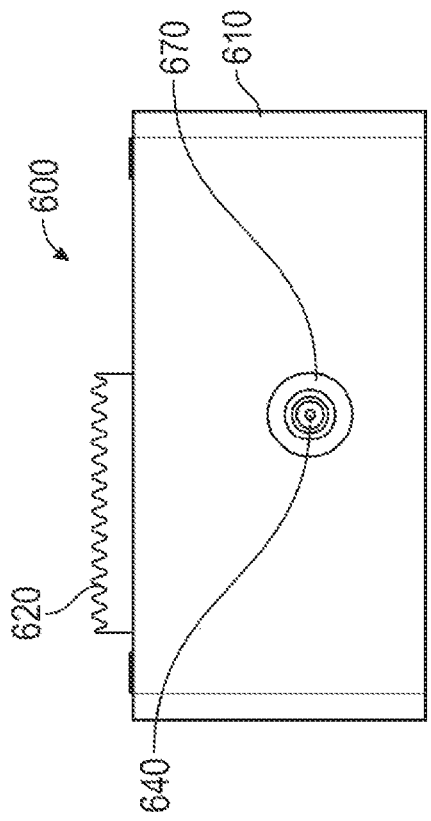
Figure 14A:
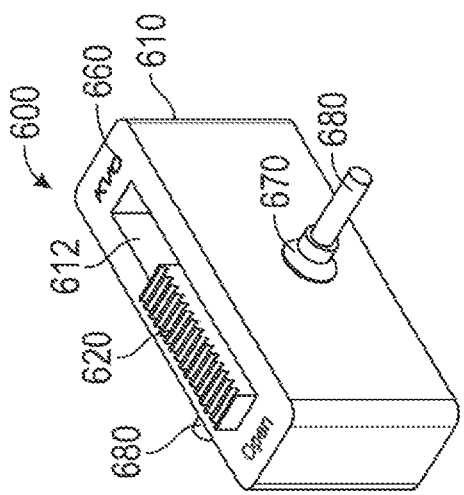
Figure 14B:
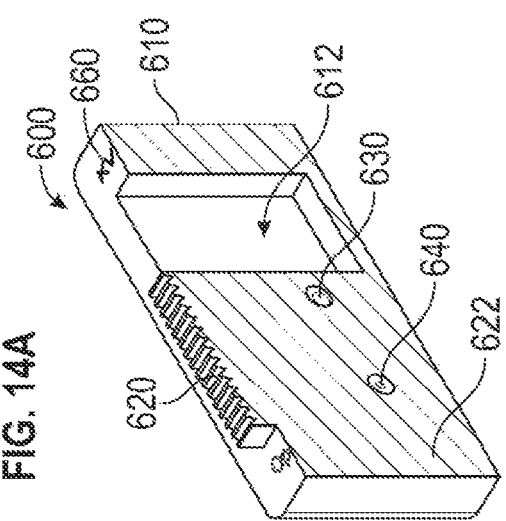
Figure 15A:
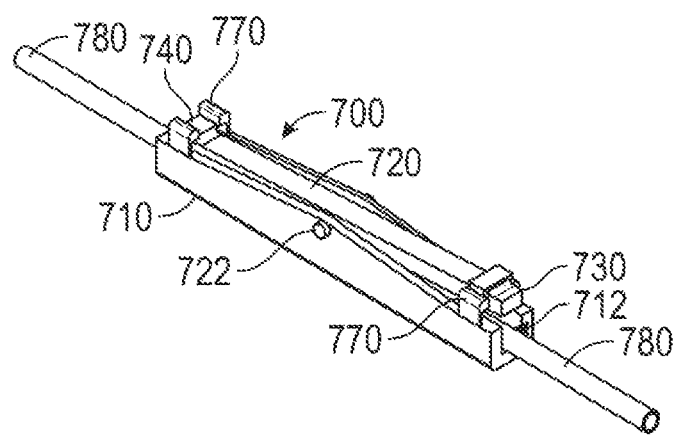
FIGS. 15A-15G are various views of a KVO infusion fluid flow control device, according to some aspects of the disclosure.
Figure 15B:
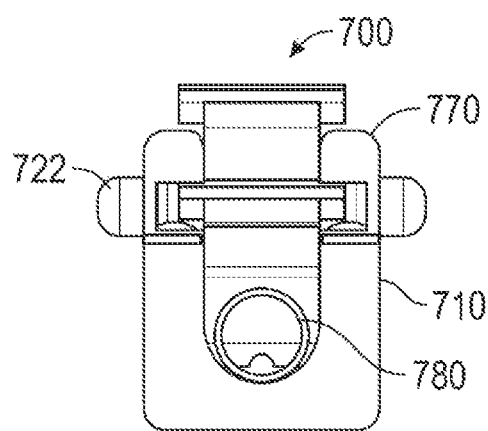
Figure 15C:
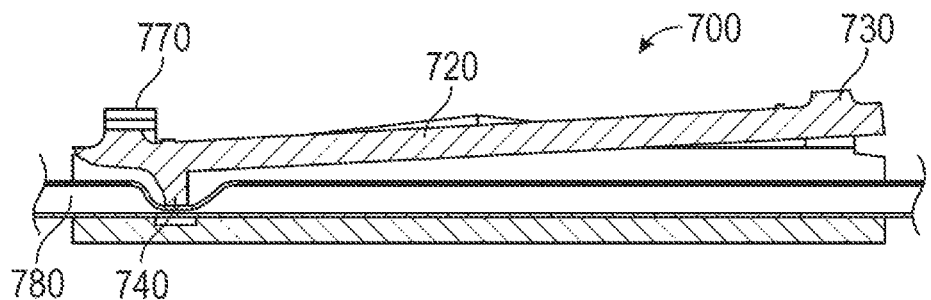
Figure 15D:
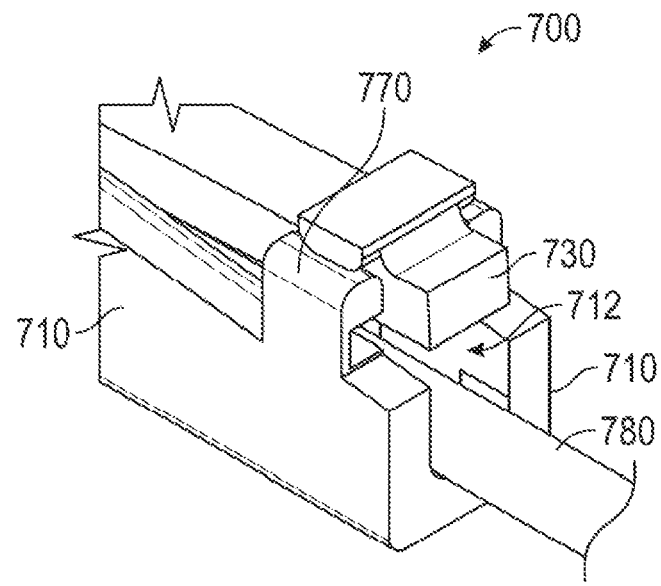
Figure 15E:
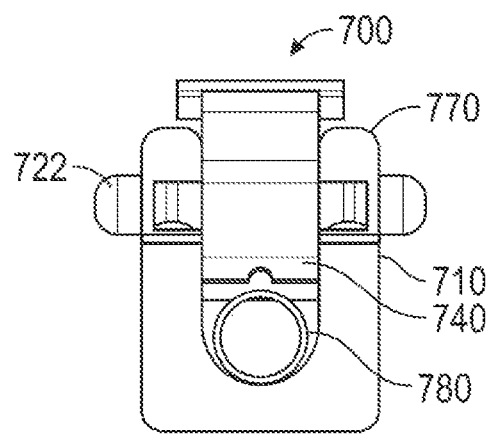
Figure 15F:
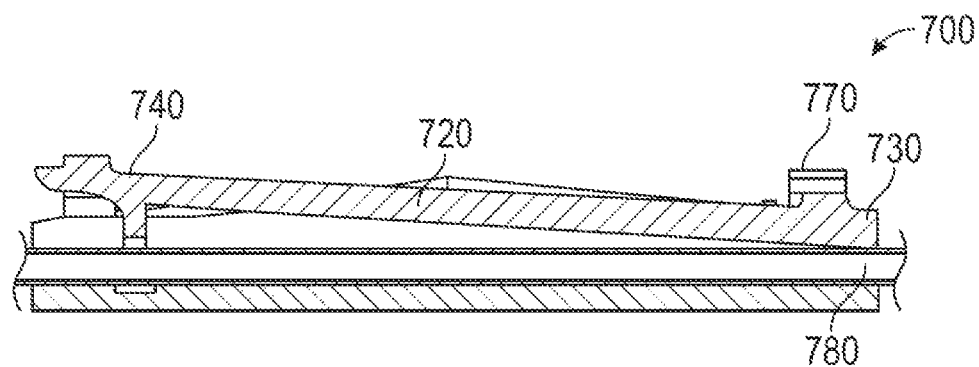
Figure 15G:
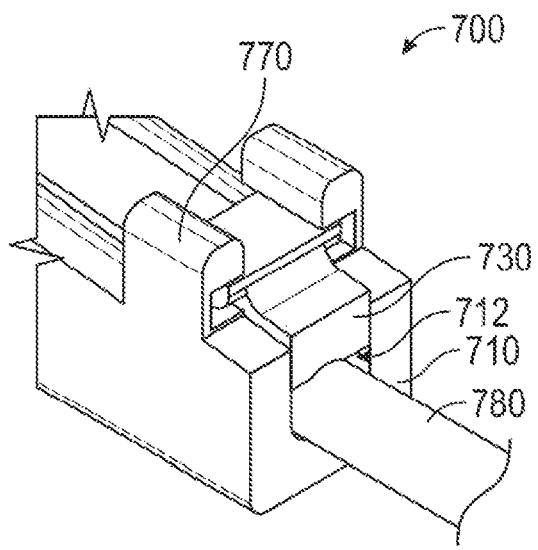
Figure 16A:
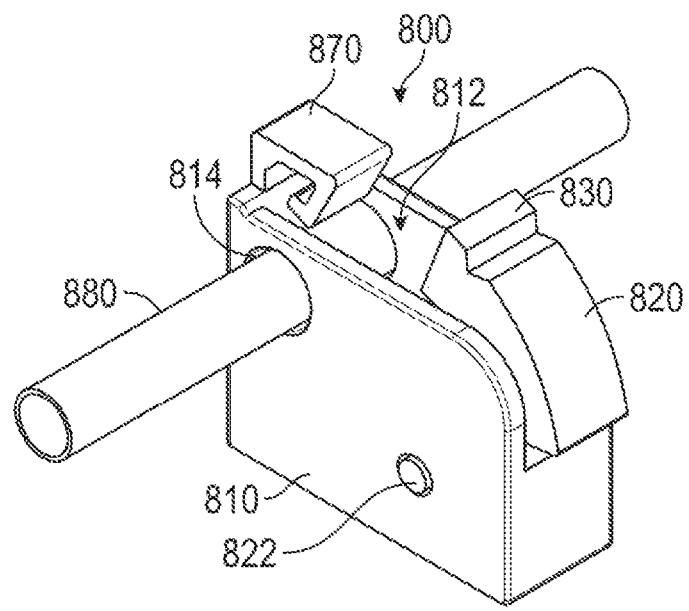
FIGS. 16A-16D are various views of a KVO infusion fluid flow control device, according to some aspects of the disclosure.
Figure 16B:
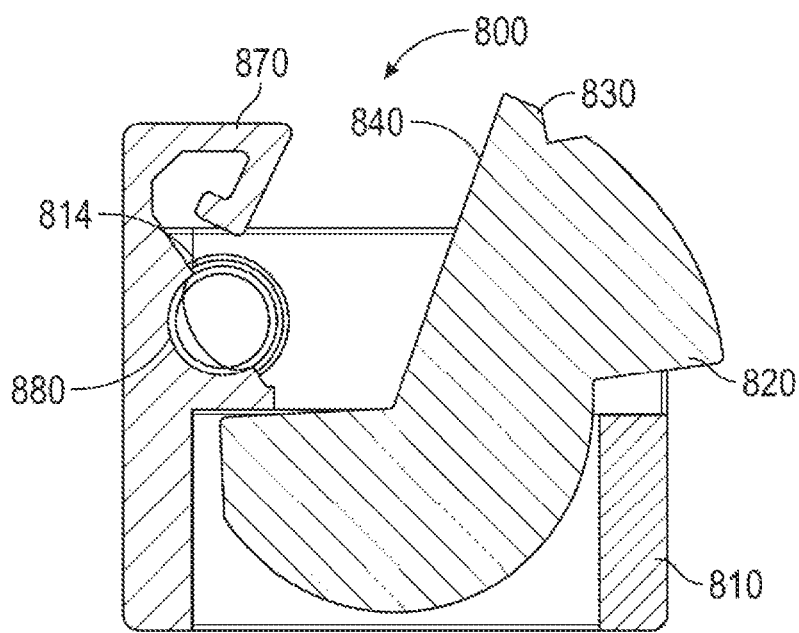
Figure 16C:
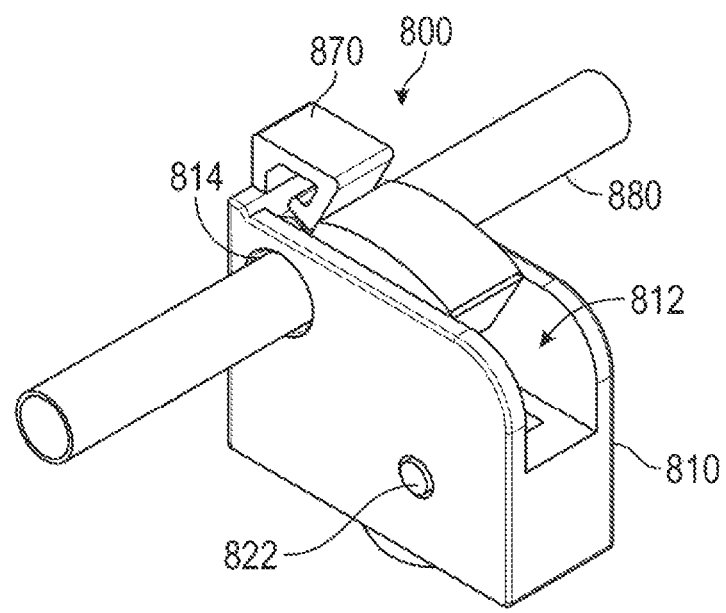
Figure 16D:
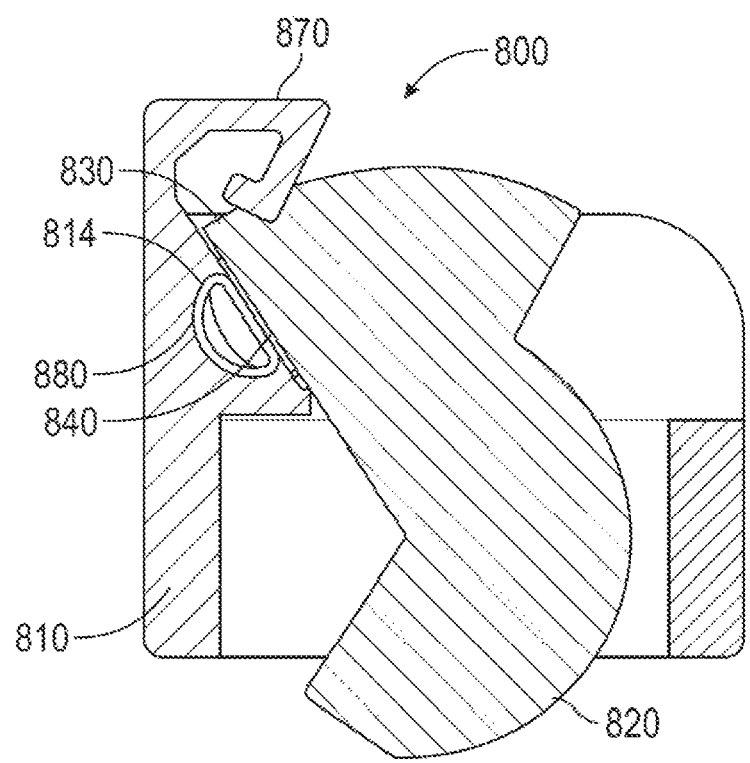
Figure 17A:
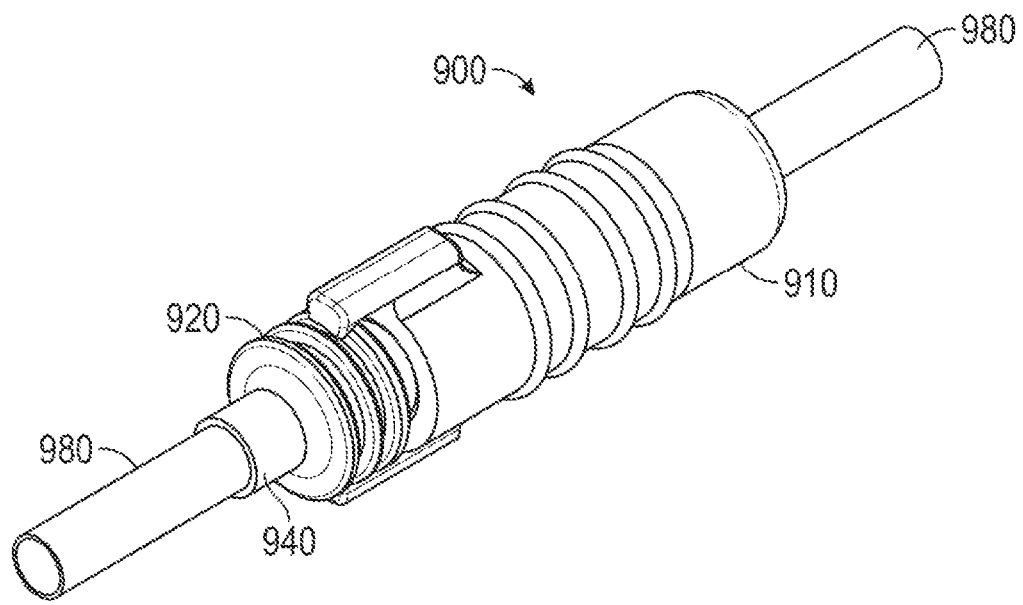
FIGS. 17A-17F are various views of a KVO infusion fluid flow control device, according to some aspects of the disclosure.
Figure 17B:
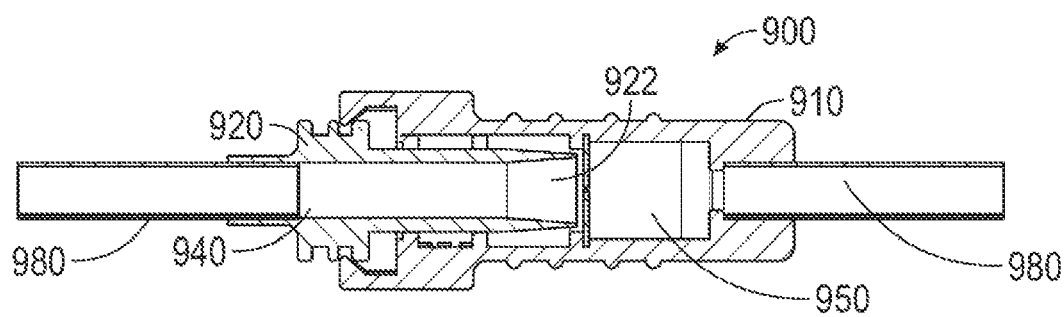
Figure 17C:
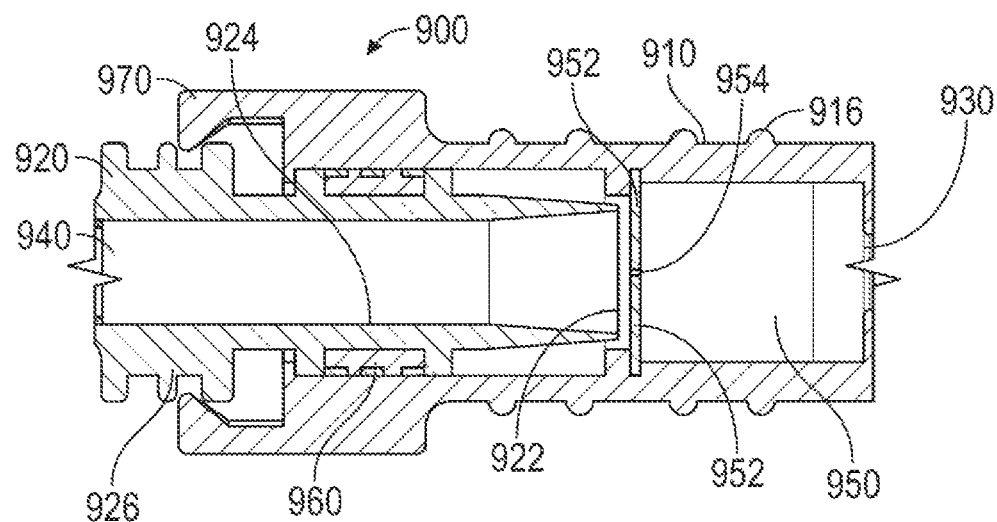
Figure 17D:
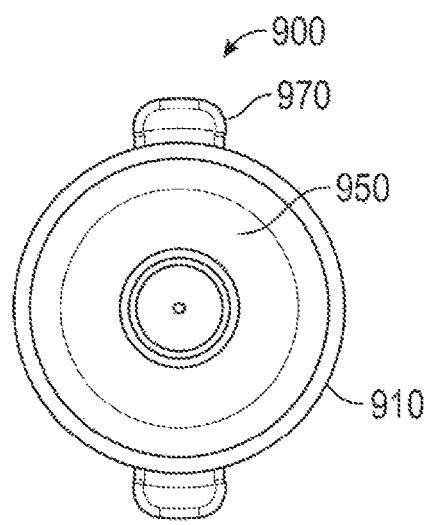
Figure 17E:
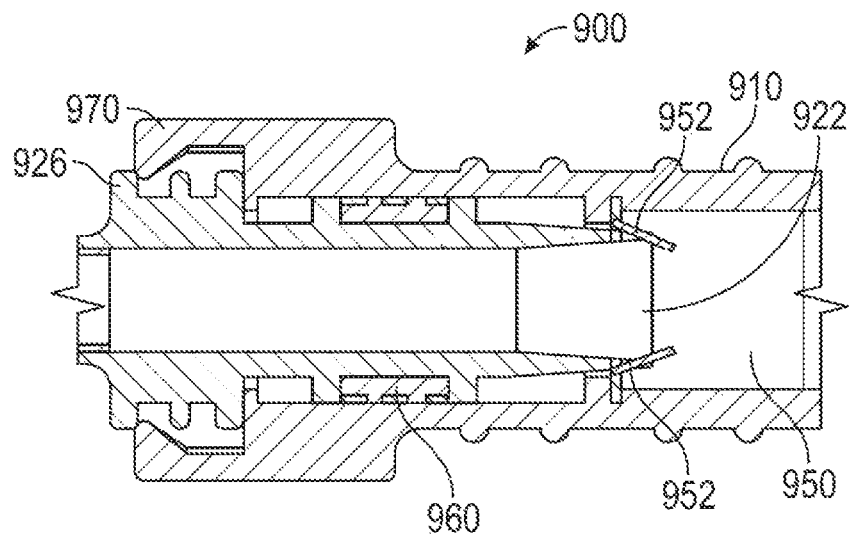
Figure 17F:
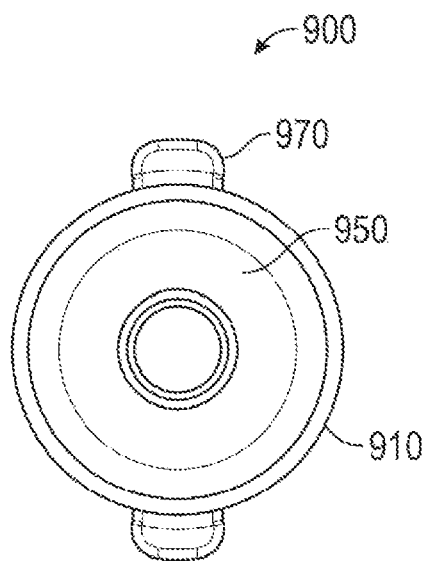

FIG. 9 is an internal view of a modeled static fluid flow profile through the KVO infusion flow control device 100 in the fully open position. As shown, even when the vast majority of the fluid flows through the full flow tube 110 when the flow controller 170 is in the open position, a portion of the fluid still flows through the KVO flow tube 120 and through the flow control orifice 180. Thus, the fluid flows from the full flow tube 110 and the flow control orifice 180 combine together in the outlet tube connector 140 and the combined fluid flow exits the outlet connector 160 at a full flow rate. By contrast, when the flow controller 170 is in the closed position, the fluid flow through the full flow tube 110 is cut off and the only fluid flow into the outlet tube connector 140 comes from the flow control orifice 180, which then exits the outlet connector 160 at the KVO flow rate.

In operation, the KVO infusion flow control device 100 sets an IV set to open when the KVO infusion flow control device 100 is in the open position (e.g., not occluded), thus allowing for full fluid flow as seen in FIGS. 2, 3 and 9. When the KVO infusion flow control device 100 is in the closed position (e.g., occluded), the KVO infusion flow control device 100 immediately sets the IV set to the KVO flow rate. Thus, the KVO infusion flow control device 100 may function as a binary full flow/KVO flow rate switch that may be easily operated (e.g., one handed operation) and is easily visualized as being in either the open flow position or the KVO flow position (e.g., pinch clamp open or closed). Further, the KVO infusion flow control device 100 provides that no further interaction with other IV set components (e.g., roller clamp, flow controller) is necessary to regulate between full open flow and KVO flow. Thus, the simplified flow control operation of the KVO infusion flow control device 100 frees up time for a user (e.g., clinician, health care provider) to perform other care related tasks, while providing an intuitive and straightforward way to set the flow rate of the IV set with minimal operation or interaction.

In aspects of the disclosure, the KVO infusion flow control device 100 provides for immediate feedback to the user when the flow controller 170 is activated (e.g., closed), as well as allowing for single handed operation by the user. The KVO infusion flow control device 100 also provides simplified control over functionality of the IV set by providing for quick and precise adjustment between open flow and KVO flow rates. The KVO infusion flow control device 100 may be attached as part of an extension set stock keeping unit (SKU) and provides the user with familiar IV set components (e.g., pinch clamp, Luer connectors).

In some aspects of the disclosure, a KVO infusion flow control device 200 is configured as a stopcock device as shown in FIGS. 10A-10E. The KVO infusion flow control device 200 includes a body 210 having a full open orifice 220 and a KVO orifice 230. An open control arm 240 and a KVO control arm 250 are coupled to the body 210. Visual indicators 260 are disposed on the open control arm 240 and KVO control arm 250. The body 210 is coupled to a fluid flow housing 270 having connectors 272 configured to receive IV tubes 280 for fluid inlet and fluid outlet.

In operation, the KVO infusion flow control device 200 may be controlled by grasping and turning the open control arm 240 and/or the KVO control arm 250 to cause one of the full open orifice 220 and the KVO orifice 230 to be in line with the fluid flow path, which causes the KVO infusion flow control device 200 to operate between a full open flow rate and a KVO flow rate. In some aspects of the disclosure, the KVO infusion flow control device 200 has no off setting for completely shutting off the flow rate.

In some aspects of the disclosure, a KVO infusion flow control device 300 is configured as a stopcock device as shown in FIGS. 11A-11D. The KVO infusion flow control device 300 includes a body 310 having a full open orifice 320 and a KVO orifice 330. An open control arm 340 and a KVO control arm 350 are coupled to the body 310. Visual indicators 360 are disposed on the open control arm 340 and KVO control arm 350. The body 310 is coupled to a fluid flow housing 370 having connectors 372 configured to receive IV tubes 380 for fluid inlet and fluid outlet. A flange 374 may be disposed around the connector 372 so that the tube 380 is received between the connector 372 and the flange 374.

In operation, the KVO infusion flow control device 300 may be controlled by grasping and turning the open control arm 340 and/or the KVO control arm 350 to cause one of the full open orifice 320 and the KVO orifice 330 to be in line with the fluid flow path, which causes the KVO infusion flow control device 300 to operate between a full open flow rate and a KVO flow rate. In some aspects of the disclosure, the KVO infusion flow control device 300 has no off setting for completely shutting off the flow rate.

In some aspects of the disclosure, a KVO infusion flow control device 400 is configured as a stopcock device as shown in FIGS. 12A-12D. The KVO infusion flow control device 400 includes a body 410 having a full open orifice 420 and a KVO orifice 430. A control switch 440 is coupled to the body 410, the control switch 440 configure to turn the body 410 between an open position and a KVO position. Visual indicators 460 are disposed on the control switch 440. The body 410 is coupled to a fluid flow housing 470 having connectors 472 configured to receive IV tubes 480 for fluid inlet and fluid outlet.

In operation, the KVO infusion flow control device 400 may be controlled by grasping and turning the control switch 440 to cause one of the full open orifice 420 and a KVO orifice 430 to be in line with the fluid flow path, which causes the KVO infusion flow control device 400 to operate between a full open flow rate and a KVO flow rate. In some aspects of the disclosure, the KVO infusion flow control device 400 has no off setting for completely shutting off the flow rate.

In some aspects of the disclosure, a KVO infusion flow control device 500 is configured as a roller clamp device as shown in FIGS. 13A-13G. The KVO infusion flow control device 500 includes a body 510 and a cam 520 slidably disposed in cam channels 512 in the body 510. A ramp 514 is disposed at a base of a tube channel 516 in the body 510, the tube channel 516 configured to receive an IV tube 580. Visual indicators 560 are disposed on the body 510.

In operation, the KVO infusion flow control device 500 may be controlled by pushing/pulling the cam 520 along the tube channel 516 of the body 510 to cause the cam 520 to engage with and impinge IV tubing 580 between the cam 520 and the ramp 514 of the body 510. Positioning the cam 520 in a fully open position causes the cam 520 to not occlude (e.g., deform, crush) the IV tubing 530 at all, which provides a full open fluid flow rate. Positioning the cam 520 in the KVO position causes the cam 520 to occlude the IV tubing 530 enough to only allow a KVO flow rate. Thus, KVO infusion flow control device 500 operates between a full open flow rate and a KVO flow rate. In some aspects of the disclosure, the KVO infusion flow control device 500 has no off setting for completely shutting off the flow rate.

In some aspects of the disclosure, a KVO infusion flow control device 600 is configured as a slide switch device as shown in FIGS. 14A-14D. The KVO infusion flow control device 600 includes a body 610 and a switch 620 slidably disposed in a switch channel 612 in the body 610. The switch 620 includes a full open channel 630 and a KVO channel 640 each disposed through the entire width of a switch housing 622. Connectors 670 are disposed on opposing sides of the body 610, the connectors 670 configured to receive IV tubes 680. Visual indicators 660 are disposed on the body 610.

In operation, the KVO infusion flow control device 600 may be controlled by pushing/pulling the switch 620 in the switch channel 612 of the body 610 to align either the full open channel 630 or the KVO channel 640 with the connectors 670. Positioning the switch 620 in a fully open position causes the switch 620 to align the full open channel 630 with the connectors 670 and correspondingly the IV tubes 680, which provides a full open fluid flow rate. Positioning the switch 620 in the KVO position causes the switch 620 to align the KVO channel 640 with the connectors 670 and correspondingly the IV tubes 680, which only allows a KVO flow rate. Thus, KVO infusion flow control device 600 operates between a full open flow rate and a KVO flow rate. In some aspects of the disclosure, the KVO infusion flow control device 600 has no off setting for completely shutting off the flow rate. In some aspects of the disclosure, the KVO infusion flow control device 600 may allow for completely shutting off the flow rate (e.g., the switch 620 is positioned such that neither the full open channel 630 nor the KVO channel 640 are aligned with the connectors 670).

In some aspects of the disclosure, a KVO infusion flow control device 700 is configured as a rocker adapter device as shown in FIGS. 15A-15G. The KVO infusion flow control device 700 includes a body 710 and a rocker switch 720 having a switch axle 722 pivotably disposed in a tube channel 712 of the body 710. An open engagement member 730 is disposed at one end of the rocker switch 720 and is sized and shaped so as not to occlude (e.g., deform, crush) IV tubing 780 disposed in the tube channel 712. A KVO engagement member 740 is disposed at the other end of the rocker switch 720 and is sized and shaped to occlude IV tubing 780 to a predetermined degree when pressed into an activated position. Retaining clips 770 are disposed on both ends of the body 710 and are configured to engage and retain whichever of the open engagement member 730 and the KVO engagement member 740 is activated (e.g., pressed into the tube channel 712). Visual indicators 760 are disposed on the body 710.

In operation, the KVO infusion flow control device 700 may be controlled by pushing one end of the rocker switch 720 to cause the corresponding open engagement member 730 or KVO engagement member 740 to press down into the tube channel 712 in which the IV tubing 780 is disposed. Pushing the rocker switch 720 on the open end causes the open engagement member 730 to either not engage with the IV tubing 780 at all or to engage with but not occlude the IV tubing 780, which provides a full open fluid flow rate. Here, the open engagement member 730 is captured and retained by the retaining clips 770 disposed on the open end. Pushing the rocker switch 720 on the KVO end causes the KVO engagement member 740 to engage with and occlude the IV tubing 780 enough to only allow a KVO flow rate. Here, the KVO engagement member 740 is captured and retained by the retaining clips 770 disposed on the KVO end. Thus, KVO infusion flow control device 700 operates between a full open flow rate and a KVO flow rate. In some aspects of the disclosure, the KVO infusion flow control device 700 has no off setting for completely shutting off the flow rate.

In some aspects of the disclosure, a KVO infusion flow control device 800 is configured as a rocker adapter device as shown in FIGS. 16A-16D. The KVO infusion flow control device 800 includes a body 810 and a rocker switch 820 having a switch axle 822 pivotably disposed in a switch channel 812 of the body 810. A tube channel 814 is disposed in the body 810 and is configured to receive an IV tube 880. A clip engagement member 830 is disposed on the rocker switch 820 and is sized and shaped to engage with and be retained by a retaining clip 870 disposed on the body 810. An engagement surface 840 is disposed on the rocker switch 820 and is configured to engage with and occlude the IV tubing 880 to a predetermined degree when the rocker switch 820 is pressed into an activated position. Visual indicators (not shown) may be disposed on the body 810.

In operation, the KVO infusion flow control device 800 may be controlled by pushing/pulling the rocker switch 820 into an open position to move the engagement surface 840 away from the tube channel 814 in which the IV tubing 880 is disposed, causing the engagement surface 840 to either not engage with the IV tubing 880 at all or to engage with but not occlude the IV tubing 880, which provides a full open fluid flow rate through the IV tubing 880. The KVO infusion flow control device 800 may also be controlled by pushing/pulling the rocker switch 820 into a KVO position to move the engagement surface 840 toward the tube channel 814 in which the IV tubing 880 is disposed, causing the engagement surface 840 to engage with and occlude the IV tubing 880 a determined amount, thus only allowing a KVO fluid flow rate through the IV tubing 880. Here, the clip engagement member 830 is captured and retained by the retaining clip 870 to hold it in the KVO (e.g., activated) position. Thus, KVO infusion flow control device 800 operates between a full open flow rate and a KVO flow rate. In some aspects of the disclosure, the KVO infusion flow control device 800 has no off setting for completely shutting off the flow rate.

In some aspects of the disclosure, a KVO infusion flow control device 900 is configured as an inline switch device as shown in FIGS. 17A-17F. The KVO infusion flow control device 900 includes a body 910 and a switch 920 slidably engaged with the body 910. The body 910 includes a body connector 930 and the switch 920 includes a switch connector 940, each sized and shaped to receive IV tubes 980. The body 910 also includes a valve 950 disposed adjacent to the body connector 930 within the body 910. The valve 950 includes valve flaps 952 that are configured to be biased towards a closed position (e.g., valve flaps 952 aligned orthogonally to an axial fluid flow channel within the body 910), which provides a KVO gap 954 between the valve flaps. The valve flaps 952 may be pivotably connected to the valve 950 (e.g., like hinged swinging doors) such that they can be pivoted open (e.g., swing open) when a leading portion 922 of the switch 920 engages and exerts a force on the valve flaps 952. The body 910 also includes a seal 960 configured to engage an exterior surface 924 of the switch 920 throughout the full range of slidable motion within the body 910, thus providing a sealing barrier preventing leakage of liquid from the KVO infusion flow control device 900. Visual indicators (not shown) may be disposed on the body 910 and/or the switch 920. The switch 920 includes switch ribs 926 and the body 910 includes body ribs 916, where the switch ribs 926 and the body ribs 916 provide for ergonomic gripping of the switch 920 and the body 910. The body 910 also includes grippers 970 disposed on an end adjacent to the switch 920, the grippers 970 configured to engage and retain a switch rib 926, thus locking a flow rate of the KVO infusion flow control device 900.

In operation, the KVO infusion flow control device 900 may be controlled by pushing/pulling the switch 920 towards/away from the valve 950. Here the leading portion 922 of the switch 920 remains within the body 910 when the switch 920 is in each of an open position and a KVO position. Pushing the switch 920 to the open setting causes the leading portion 922 to engage with the valve flaps 952 and force the valve flaps 952 to pivot inwards towards the body connector 930, thus opening a full flow path to allow an open fluid flow rate out the body connector 930 into an outlet IV tube 980. Pulling the switch 920 out to the KVO setting causes the leading portion 922 to disengage with the valve flaps 952 and allow the biasing force of the valve flaps 952 to pivot the valve flaps 952 away from the body connector 930 and to align orthogonally to an axial fluid flow channel within the body 910, thus providing the KVO gap 954 to allow only a KVO fluid flow rate out the body connector 930 into an outlet IV tube 980. Thus, KVO infusion flow control device 900 operates between a full open flow rate and a KVO flow rate. In some aspects of the disclosure, the KVO infusion flow control device 900 has no off setting for completely shutting off the flow rate.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

The invention claimed is:

1. A keep vein open (KVO) infusion flow control device, comprising:
   an inlet tube connector comprising an intravenous (IV) inlet port, a first outlet port and a second outlet port;
   an outlet tube connector comprising an IV outlet port, a first inlet port, a second inlet port and a flow control orifice disposed within the second inlet port;
   a full flow tube coupled at one end to the first outlet port of the inlet tube connector and coupled at another end to the first inlet port of the outlet tube connector;
   a KVO flow tube coupled at one end to the second outlet port of the inlet tube connector and coupled at another end to the second inlet port of the outlet tube connector; and
   a single flow controller coupled to the full flow tube, the single flow controller by itself configured to control fluid flow through the full flow tube and an amount of fluid flow through the KVO flow tube,
   wherein the KVO flow tube is configured to always provide some fluid flow.

2. The KVO infusion flow control device of claim 1, wherein the flow controller is configured to provide full fluid flow through the full flow tube into the outlet tube connector when the flow controller is disposed in a first position that does not occlude the full flow tube.

3. The KVO infusion flow control device of claim 1, wherein the flow controller is configured to shut off fluid flow through the full flow tube into the outlet tube connector when the flow controller is disposed in a second position that occludes the full flow tube to a predetermined degree.

4. The KVO infusion flow control device of claim 3, wherein the flow control orifice is configured to limit fluid flow into the outlet tube connector when the flow controller is disposed in the second position.

5. The KVO infusion flow control device of claim 4, wherein the flow control orifice is sized and shaped to provide a predetermined KVO fluid flow rate into the outlet tube connector when the flow controller is disposed in the second position.

6. The KVO infusion flow control device of claim 1, further comprising an inlet connector coupled to the IV inlet port, the inlet connector configured to be coupled to an inlet IV tube.

7. The KVO infusion flow control device of claim 6, further comprising an outlet connector coupled to the IV outlet port, the outlet connector configured to be coupled to an outlet IV tube.

8. The KVO infusion flow control device of claim 1, wherein the flow control orifice comprises a tube engagement portion disposed within an internal diameter of the KVO flow tube.

9. The KVO infusion flow control device of claim 8, wherein the flow control orifice further comprises a restriction portion disposed adjacent to the tube engagement portion, the restriction portion configured to block fluid flow from the tube engagement portion into the outlet tube connector.

10. The KVO infusion flow control device of claim 9, wherein the flow control orifice further comprises a flow portion disposed within the restriction portion, the flow portion configured to restrict fluid flow into the outlet tube connector to a KVO fluid flow rate.

11. The KVO infusion flow control device of claim 1, wherein the flow controller is a pinch clamp.

12. A keep vein open (KVO) infusion flow control device, comprising:
   a body comprising a full open orifice disposed through the body and a separate smaller KVO orifice disposed through the body at an angle to the full open orifice;
   a control member coupled to the body; and
   a visual indicator,
   wherein a first position of the control member is configured to engage the full open orifice with a fluid flow path to provide full fluid flow through an intravenous (IV) tube and a second position of the control member is configured to engage the KVO orifice with the fluid flow path to provide KVO fluid flow through the same IV tube.

13. The KVO infusion flow control device of claim 12, wherein the control member comprises:
   an open control arm having a first visual indicator disposed thereon, the open control arm parallel to the full open orifice; and
   a KVO control arm having a second visual indicator disposed thereon, the KVO control arm parallel to the KVO orifice,
   wherein the body is rotatably coupled to a fluid flow housing, the fluid flow housing including an inlet connector configured to receive a fluid inlet IV tube at one end of the fluid flow housing and an outlet connector configured to receive a fluid outlet IV tube at an opposing end of the fluid flow housing.

14. The KVO infusion flow control device of claim 13, further comprising a first flange disposed circumferentially around a portion of the inlet connector and a second flange disposed circumferentially around a portion of the outlet connector, wherein the fluid inlet IV tube is received in a gap between the first flange and the inlet connector and the fluid outlet IV tube is received in a gap between the second flange and the outlet connector.

15. The KVO infusion flow control device of claim 12, wherein the control member comprises:
   a circular control switch comprising:
      a first visual indicator disposed on a top surface;
      a gripping extension disposed on the top surface, the gripping extension parallel to the KVO orifice; and
      a second visual indicator disposed on a top surface of the gripping extension,
   wherein the body is rotatably coupled to a fluid flow housing, the fluid flow housing configured to receive a fluid inlet IV tube at one end of the fluid flow housing and to receive a fluid outlet IV tube at an opposing end of the fluid flow housing.

16. A keep vein open (KVO) infusion flow control device, comprising:
a body;
a switch movably coupled to the body between a full open flow position and a separate KVO flow position; and
a visual indicator,
wherein a first position of the switch is configured to engage a full open orifice with a fluid flow path to provide full fluid flow through intravenous (IV) tubing and a second position of the switch is configured to engage a KVO orifice with the fluid flow path to provide KVO fluid flow through the same IV tubing, the KVO orifice being smaller than the full open orifice.

17. The KVO infusion flow control device of claim 16, wherein the switch comprises a slide switch disposed within a switch channel in the body,
wherein the IV tubing comprises a fluid inlet IV tube and a fluid outlet IV tube,
wherein the body is configured to receive the fluid inlet IV tube at a first connector disposed on a side wall of the body and to receive the fluid outlet IV tube at a second connector disposed on an opposing side wall of the body,
wherein a full open channel is disposed through a width of the slide switch and is aligned with the first and second connectors in the first position, and
wherein a KVO channel is disposed through the width of the slide switch and is aligned with the first and second connectors in the second position.

18. The KVO infusion flow control device of claim 16, wherein the switch comprises a rocker switch pivotably disposed in a tube channel of the body,
wherein a first portion of the rocker switch is an open engagement member sized and shaped to engage the IV tubing such that the IV tubing is not occluded when the rocker switch is in the first position, and
wherein a second portion of the rocker switch is a KVO engagement member sized and shaped to engage the IV tubing such that the IV tubing is occluded when the rocker switch is in the second position.

19. The KVO infusion flow control device of claim 16, wherein the switch comprises a rocker switch pivotably disposed in a switch channel of the body,
wherein an engagement surface of the rocker switch does not occlude the IV tubing when the rocker switch is in the first position, and
wherein a retaining clip is disposed on the body, the retaining clip configured to hold an engagement member the rocker switch so that the IV tubing is occluded by the engagement surface when the rocker switch is in the second position.

20. The KVO infusion flow control device of claim 16, wherein the switch is slidably coupled to the body, the switch comprising:
a leading portion disposed within the body;
an exterior surface disposed within the body;
a switch rib; and
a switch connector configured to receive an inlet IV tube;
the body comprising:
a body connector configured to receive an outlet IV tube;
a valve disposed adjacent to the body connector, the valve having pivotably connected valve flaps;
a seal disposed on a portion of the exterior surface of the switch; and
a gripper,
wherein the gripper of the body retains the switch rib and the leading portion of the switch holds the valve flaps in the full open flow position when the switch is in the first position, and
wherein the leading portion of the switch is removed from engagement with the valve flaps and the valve flaps are biased in a closed position having a KVO gap when the switch is in the second position.

* * * * *